US008454599B2

(12) United States Patent
Inagaki et al.

(10) Patent No.: US 8,454,599 B2
(45) Date of Patent: Jun. 4, 2013

(54) TREATMENT APPARATUS AND ELECTRO-SURGICAL DEVICE

(75) Inventors: Genri Inagaki, Hachioji (JP); Takashi Mihori, Akiruno (JP); Akinori Kabaya, Hachioji (JP)

(73) Assignee: Olympus Medical Systems Corp. (JP)

( * ) Notice: Subject to any disclaimer, the term of this patent is extended or adjusted under 35 U.S.C. 154(b) by 1031 days.

(21) Appl. No.: 12/190,669

(22) Filed: Aug. 13, 2008

(65) Prior Publication Data
US 2010/0042101 A1 Feb. 18, 2010

(51) Int. Cl.
*A61B 18/18* (2006.01)

(52) U.S. Cl.
USPC .............. 606/50; 606/51; 606/42; 606/41

(58) Field of Classification Search
USPC .................................. 606/48–51, 40
See application file for complete search history.

(56) References Cited

U.S. PATENT DOCUMENTS

| 5,334,193 | A | * | 8/1994 | Nardella | 606/41 |
| 5,403,312 | A | * | 4/1995 | Yates et al. | 606/50 |
| 6,558,385 | B1 | | 5/2003 | McClurken et al. | 606/50 |
| 6,953,461 | B2 | | 10/2005 | McClurken et al. | 606/51 |
| 7,115,139 | B2 | | 10/2006 | McClurken et al. | 607/96 |
| 2003/0216733 | A1 | | 11/2003 | McClurken et al. | |
| 2005/0033278 | A1 | * | 2/2005 | McClurken et al. | 606/41 |

FOREIGN PATENT DOCUMENTS

| DE | 197 38 457 | 3/1999 |
| JP | 2003-235865 | 8/2003 |
| JP | 2004-8581 | 1/2004 |
| JP | 2004-8582 | 1/2004 |
| JP | 2004-8583 | 1/2004 |
| JP | 2004-500207 | 1/2004 |
| JP | 2005-525861 | 9/2005 |
| JP | 2006-506106 | 2/2006 |
| JP | 2007-075468 | 3/2007 |
| WO | WO 0166026 | 9/2001 |

OTHER PUBLICATIONS

Letter from German associate dated May 10, 2011 forwarding the Search Report dated Apr. 8, 2011 to Japanese associate, including discussion of relevancy thereof.

(Continued)

*Primary Examiner* — Nicholas Lucchesi
*Assistant Examiner* — Leah Stohr
(74) *Attorney, Agent, or Firm* — Ostrolenk Faber LLP

(57) ABSTRACT

A treatment apparatus to treat living tissues by applying energy to the living tissues, includes
  an energy source which supplies energy,
  a pair of holding faces to hold the living tissues,
  a joining treatment portion arranged in at least one of the holding faces to join the living tissues held between the holding faces,
  a detection portion which detects, through the joining treatment portion, living information of the living tissues by supplying energy to the living tissues through the joining treatment portion,
  a fluid feed portion disposed on at least one of the holding faces to feed fluid to the living tissues, and the fluid fed from the fluid feed portion guides energy to the living tissues, and
  a control portion to control a feed rate of the fluid fed from the fluid feed portion based on the living information of the living tissues detected by the detection portion.

20 Claims, 26 Drawing Sheets

OTHER PUBLICATIONS

Search Report issued by European Patent Office in connection with corresponding application No. EP 10 01 5949 on Apr. 8, 2011.
Letter from German associate dated Dec. 2, 2009 forwarding the Search Report dated Nov. 27, 2009 to Japanese associate, including discussion of relevancy thereof.

Search Report issued by European Patent Office in connection with corresponding application No. EP 09 00 9891 on Nov. 27, 2009.
Japanese Office Action mailed Dec. 4, 2012 in connection with corresponding Japanese Patent Application No. 2009-171425 and English translation thereof.

* cited by examiner

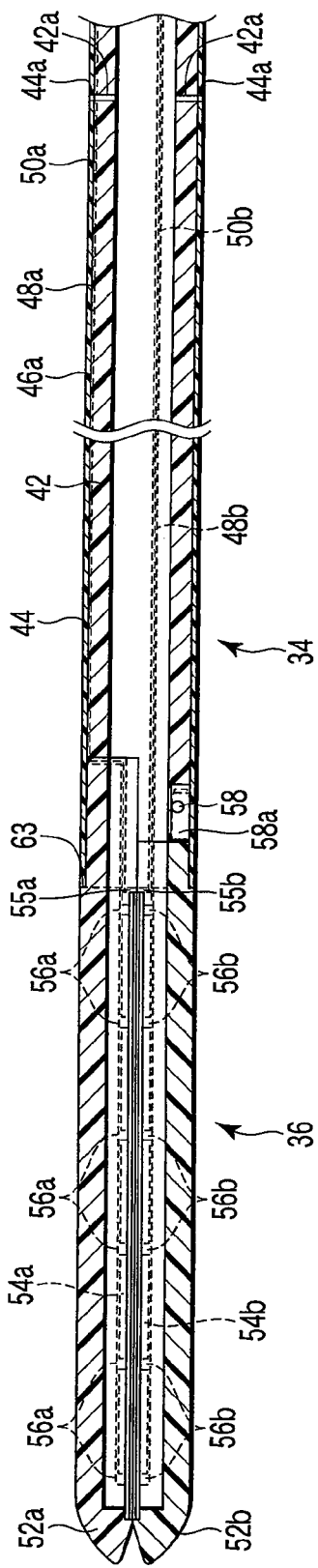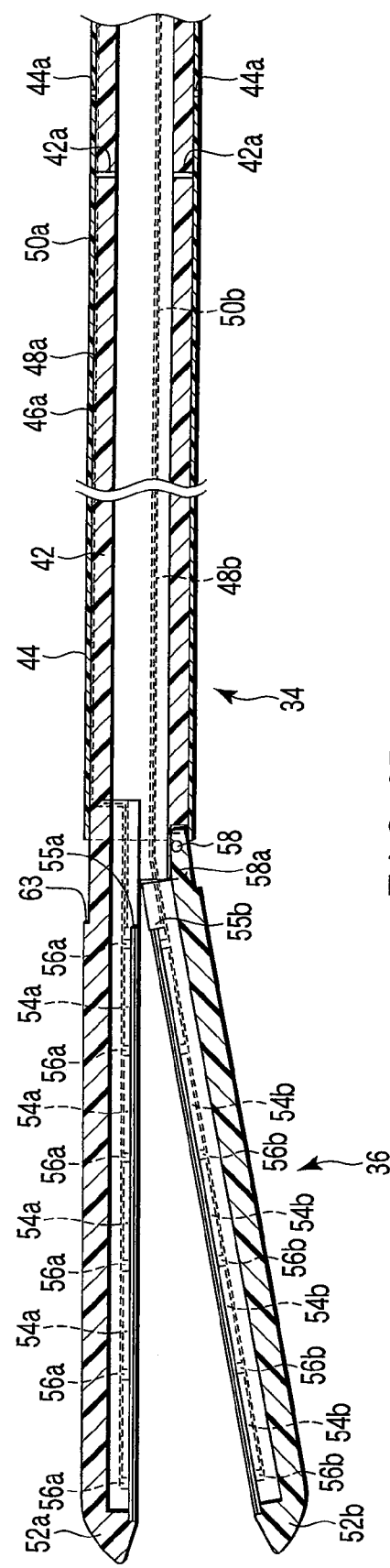
FIG. 3A
FIG. 3B

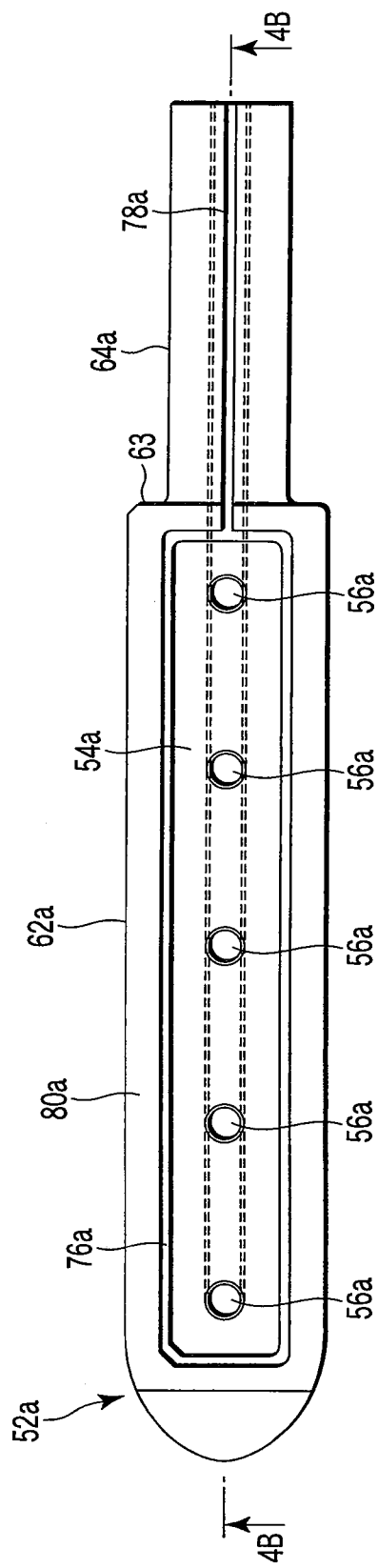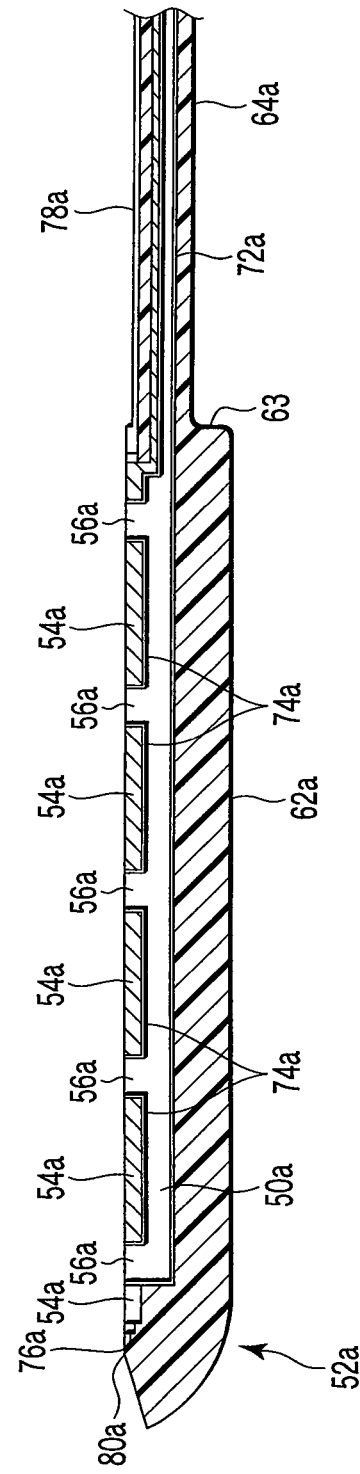
FIG. 4A
FIG. 4B

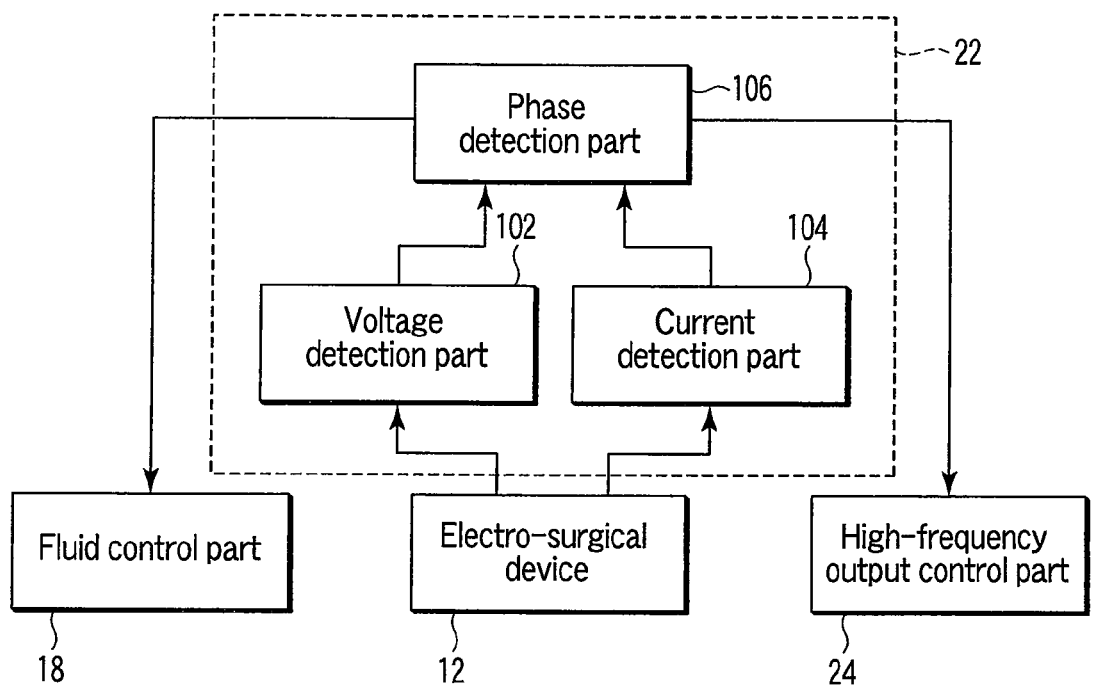
F I G. 9
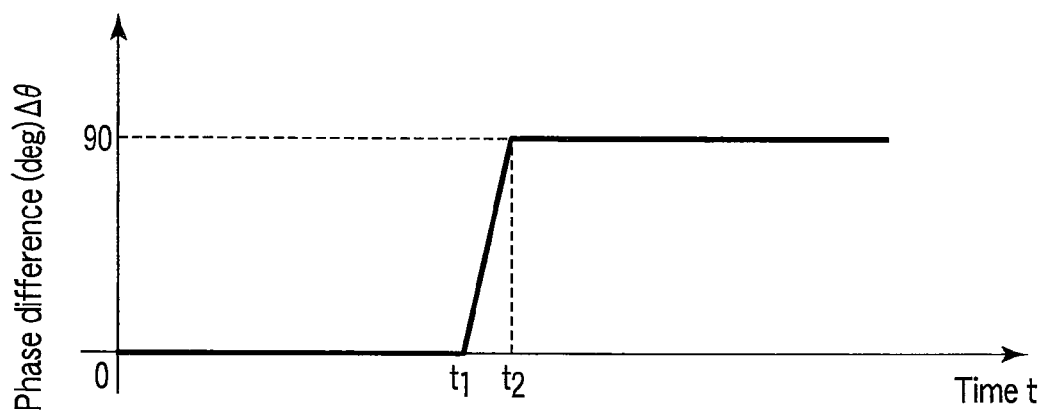
F I G. 10

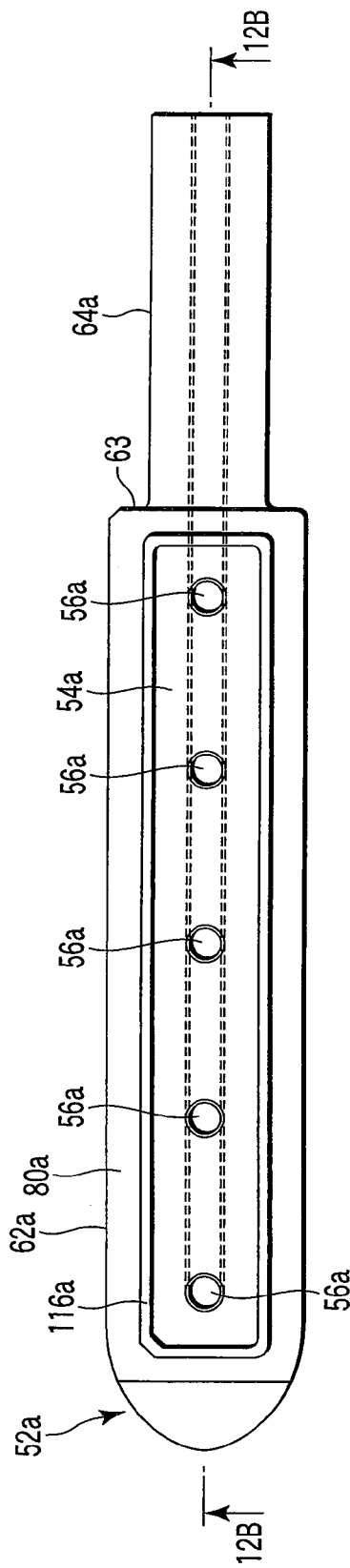
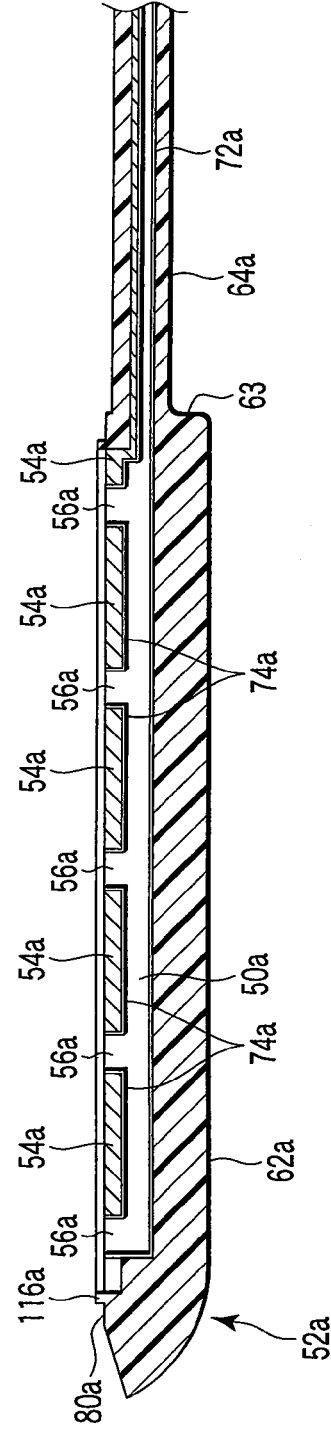
FIG. 12A
FIG. 12B

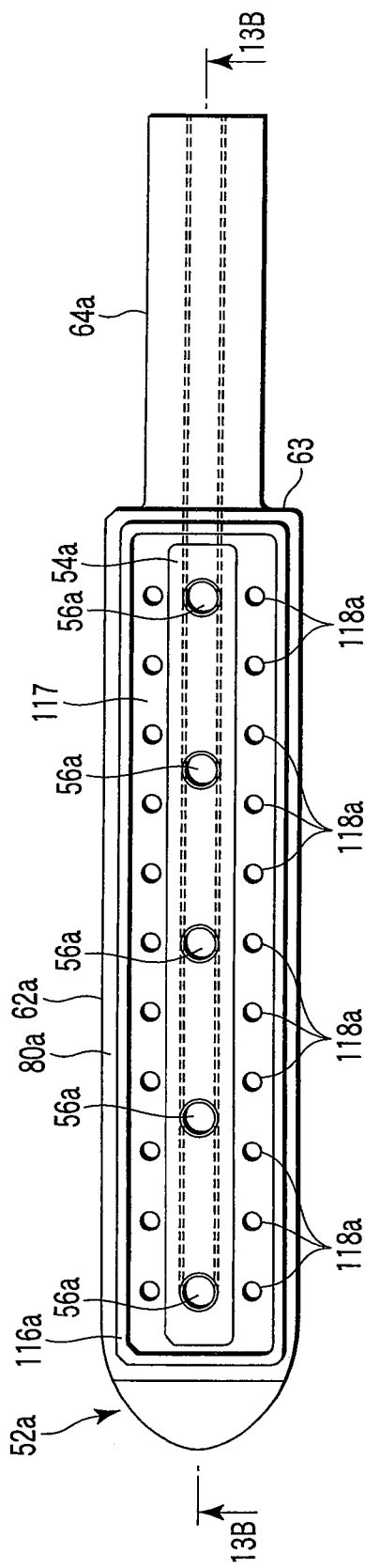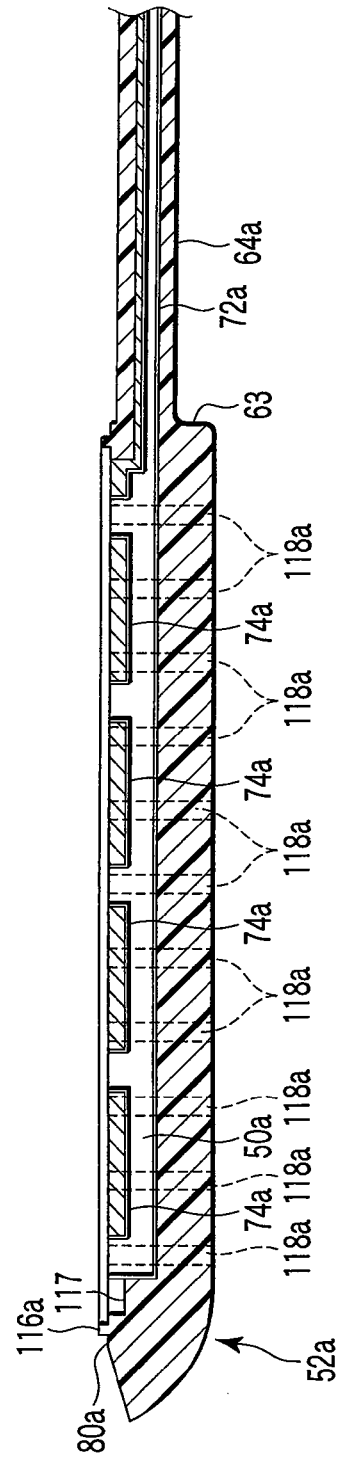
FIG. 13A
FIG. 13B

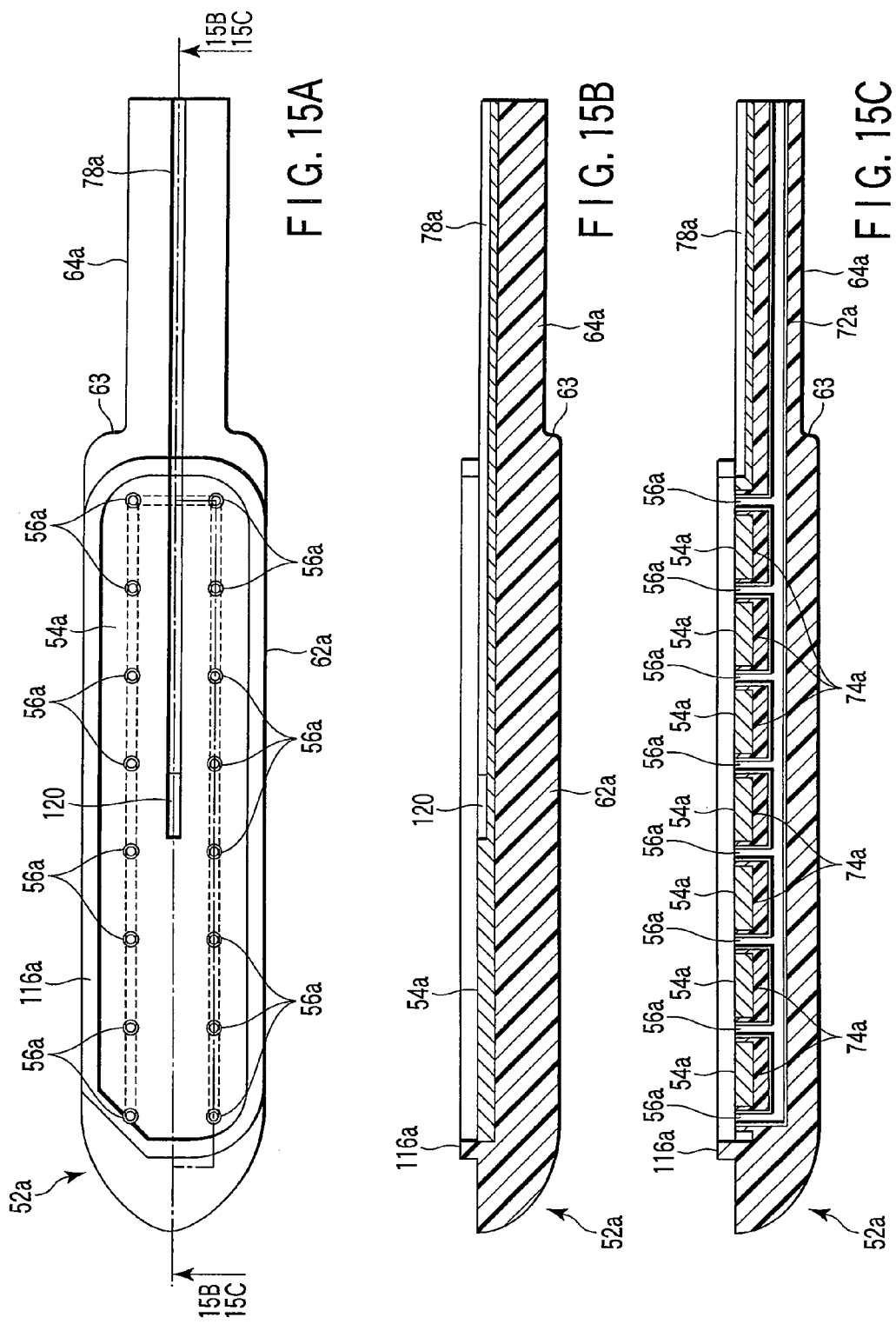

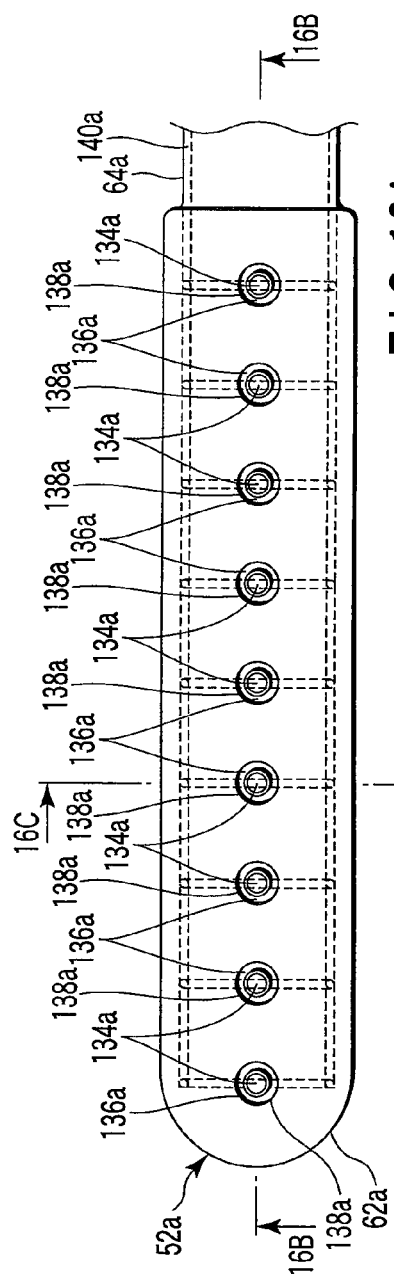
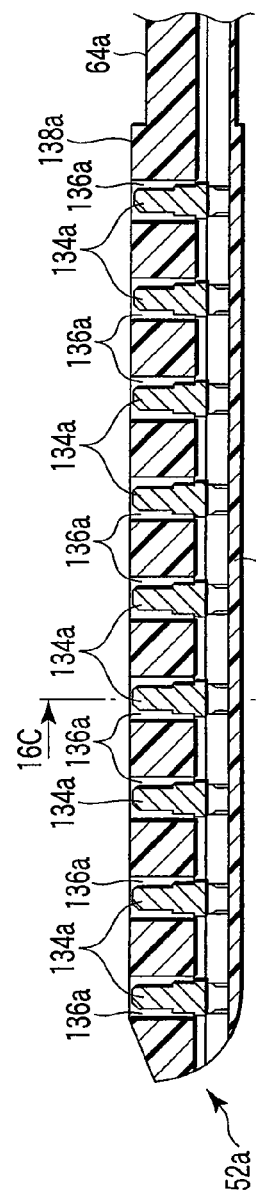
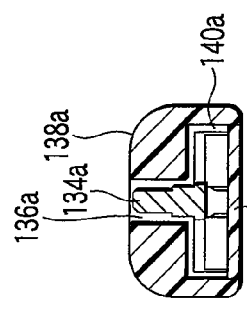
FIG. 16A
FIG. 16B
FIG. 16C

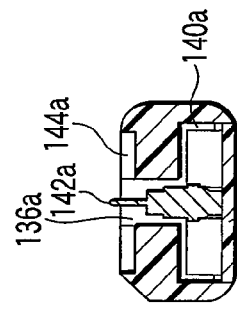
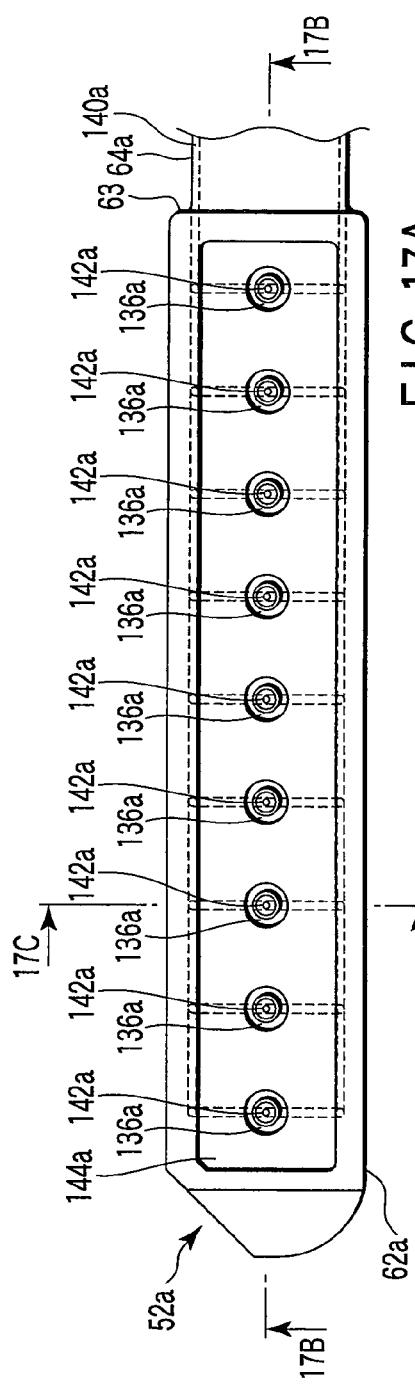
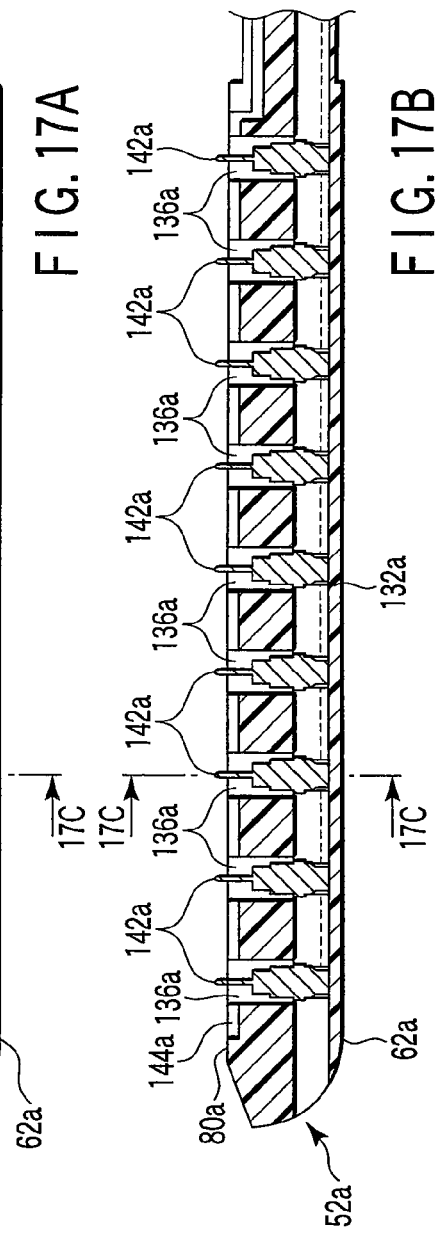

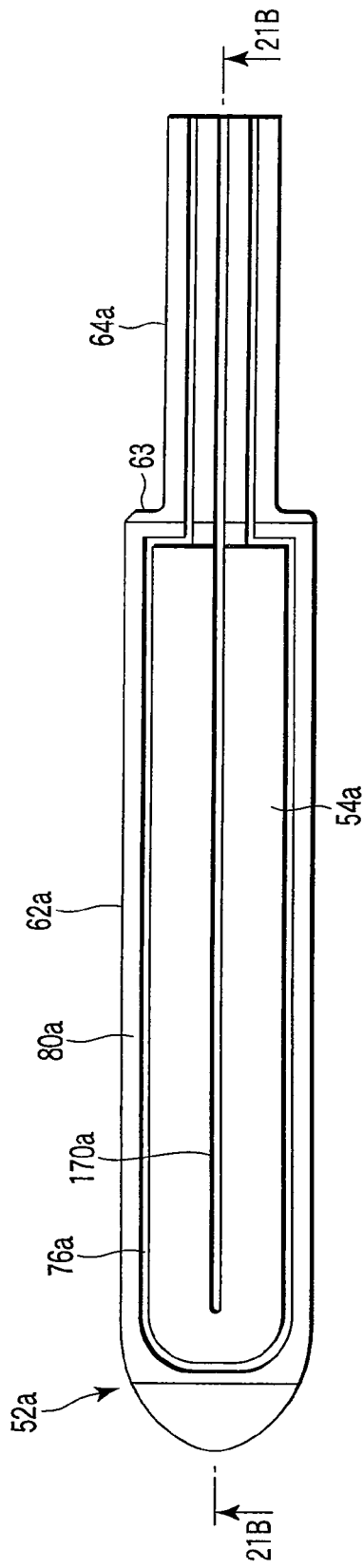
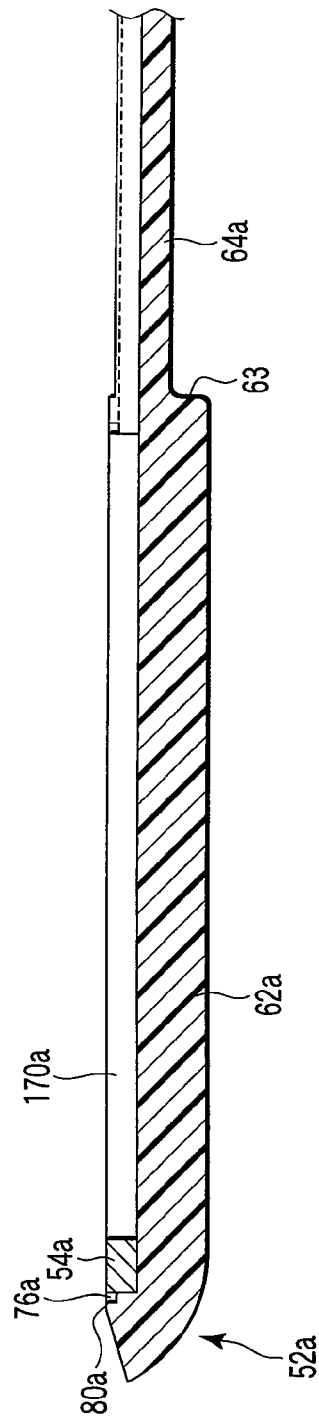
FIG. 21A
FIG. 21B

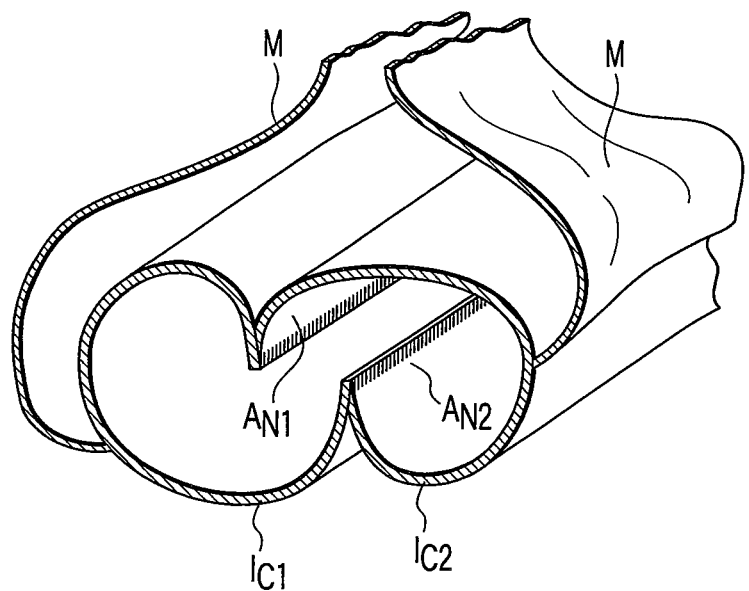
F I G. 22A
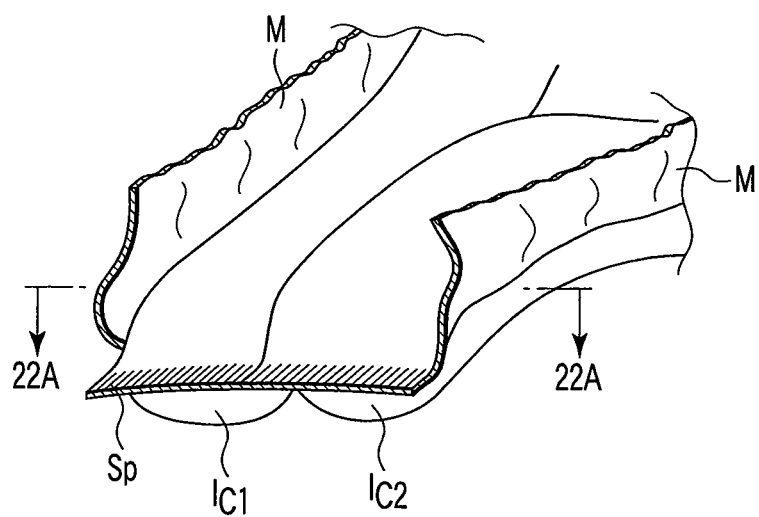
F I G. 22B

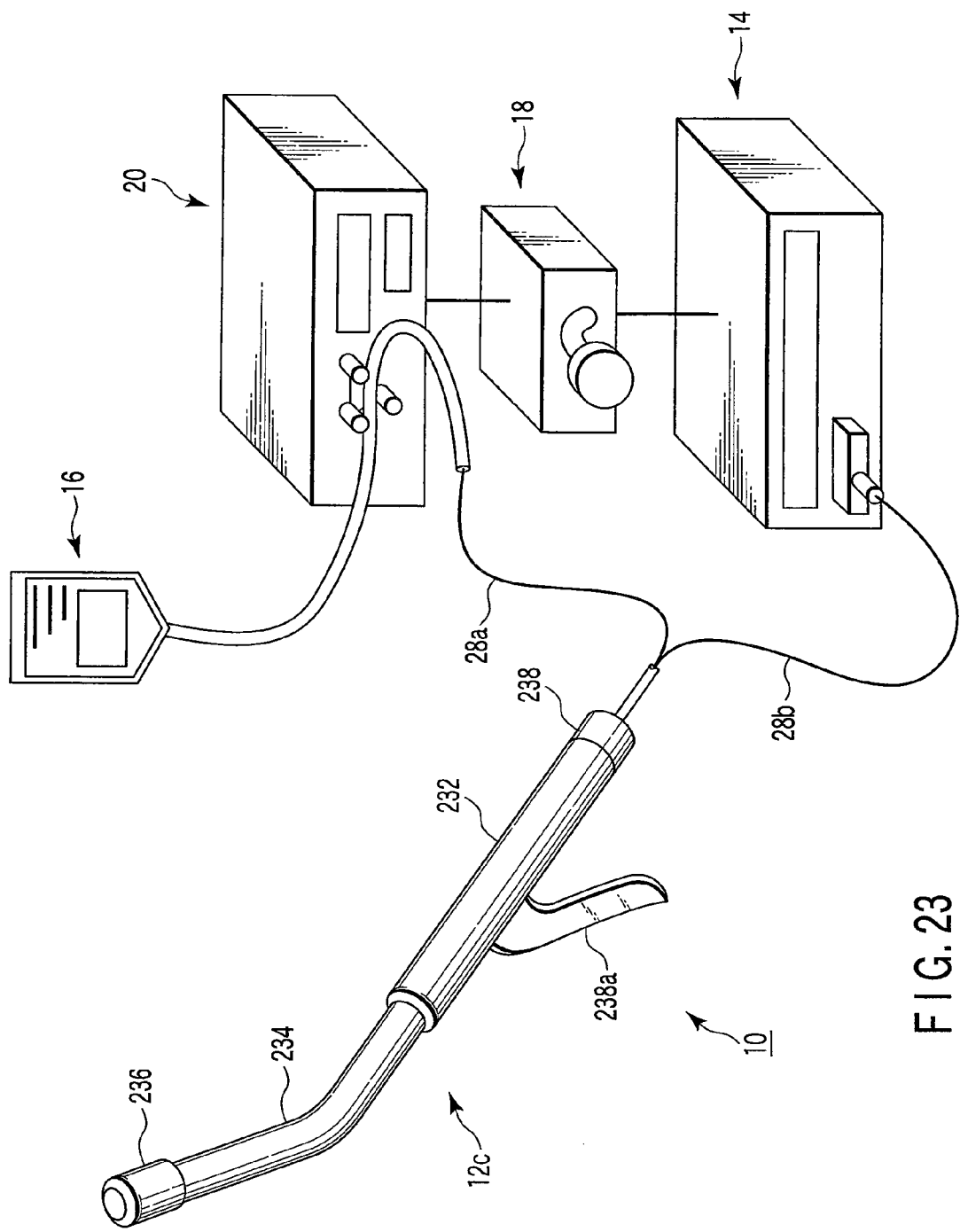
F I G. 23

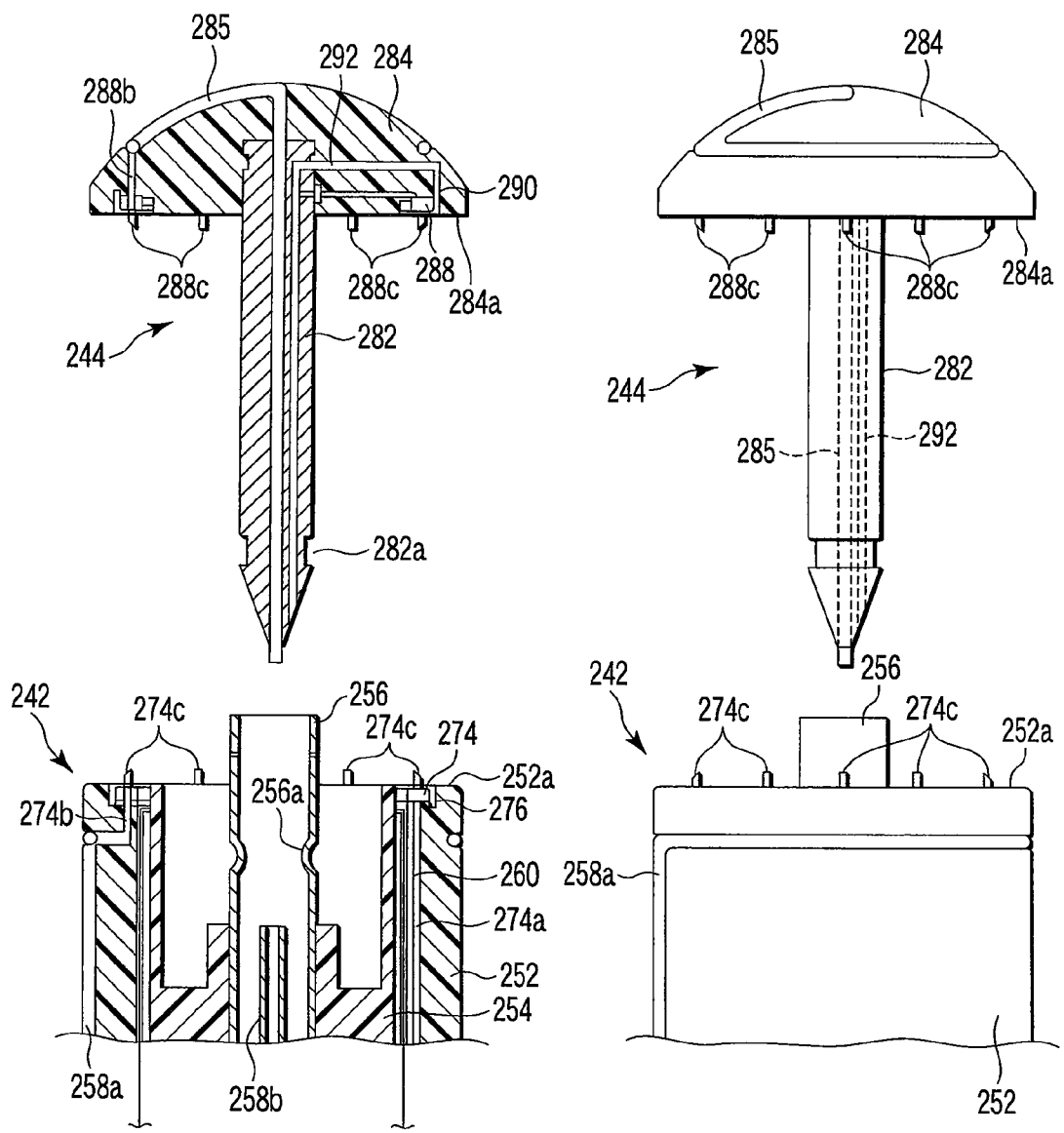
FIG. 27A                    FIG. 27B ed from the fluid feed portion guide energy to the living tissues held between the pair of holding faces; and a control portion to control a feed rate of the fluid fed from the fluid feed portion based on the living information of the living tissues detected by the detection portion.

According to a second aspect of the present invention, there is provided an electro-surgical device for joining living tissues, includes:

a pair of holding faces which hold the living tissues;

an electrode which is provided on at least one of the pair of holding faces to supply high-frequency energy to the living tissues held by the pair of holding faces and be able to detect living information of the living tissues held by the pair of holding faces; and a fluid feed portion provided on the holding face or the electrode, and being able to feed a conductive fluid to the living tissues held by the pair of holding faces.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

TREATMENT APPARATUS AND ELECTRO-SURGICAL DEVICE

BACKGROUND OF THE INVENTION

1. Field of the Invention

The present invention relates to a treatment apparatus and an electro-surgical device for joining living tissues using energy.

2. Description of the Related Art

For example, U.S. Pat. No. 7,115,139 B2 and U.S. Pat. No. 6,953,461 B2 disclose forceps capable of infusing a liquid into a living tissue while the living tissue is being coagulated by high-frequency energy. Thus, drying, carbonization, and burning of a living tissue and sticking of the tissue to forceps adversely affecting coagulation when the living tissue is coagulated by high-frequency energy can be prevented by a technology disclosed by U.S. Pat. No. 7,115,139 B2 and U.S. Pat. No. 6,953,461 B2.

Further, a control method of infusing a liquid disclosed by U.S. Pat. No. 7,115,139 B2 controls the flow rate of an electrically conducting fluid in accordance with the magnitude of output so that a desired temperature (100° C.) is reached using the cooling action of the liquid by controlling the ratio of the electrically conducting fluid removed at a boiling point.

Also, a control method of infusing a liquid disclosed by U.S. Pat. No. 6,953,461 B2 changes the flow rate of the liquid to control boiling of an electrically conducting fluid based on a signal from an output measuring device.

Further, Jpn. Pat. Appln. KOKAI Publication Nos. 2004-8581, 2004-8582, and 2004-8583 disclose a galvanosurgery apparatus for easily and reliably performing a wide range of thermocoagulation operations. The basic idea of the technology disclosed by Jpn. Pat. Appln. KOKAI Publication Nos. 2004-8581, 2004-8582, and 2004-8583 is to remedy electric characteristics of living tissues near an energizing part through enhancement of electric conductivity by supplying a wetting liquid such as a physiological salt solution to tissues through which a high-frequency current is less likely to pass because of thermocoagulation (tissue cauterization) and drying. This allows a wide range of thermocoagulation (tissue cauterization) and tissue ablation. Then, Jpn. Pat. Appln. KOKAI Publication Nos. 2004-8581, 2004-8582, and 2004-8583 disclose methods of controlling an infusion amount of liquid, such as a method of controlling the infusion amount of fluid, based on detection information such as pressure and temperature, and a method of controlling a high-frequency device and a pump based on a tissue impedance.

BRIEF SUMMARY OF THE INVENTION

According to a first aspect of the present invention, there is provided a treatment apparatus to treat living tissues by applying energy to the living tissues, includes:

an energy source which supplies energy;

a pair of holding faces to hold the living tissues;

a joining treatment portion arranged in at least one of the pair of holding faces to join the living tissues held between the pair of holding faces by energy supplied from the energy source;

a detection portion which detects, through the joining treatment portion, living information of the living tissues held between the pair of holding faces by supplying energy to the living tissues through the joining treatment portion;

a fluid feed portion disposed on at least one of the holding faces of the pair of holding faces to feed fluid to the living tissues held between the pair of holding faces, and the fluid

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a schematic longitudinal sectional view showing a shaft of an electro-surgical device of the treatment apparatus and a holding portion having first and second holding members in a state where the holding portion is closed of the electro-surgical device of the treatment apparatus according to the first to ninth embodiments;

FIG. 3B is a schematic longitudinal sectional view showing the shaft of the electro-surgical device of the treatment apparatus and the first and second holding members in a state where the holding portion is opened of the electro-surgical device of the treatment apparatus according to the first to ninth embodiments;

FIG. 4A is a schematic plan view showing the first holding member on a side nearer to the second holding member of the holding portion of the electro-surgical device of the treatment apparatus according to the first embodiment;

FIG. 4B is a schematic longitudinal sectional view showing the first holding member along a line 4B-4B shown in FIG. 4A of the holding portion of the electro-surgical device of the treatment apparatus according to the first embodiment;

FIG. 9 is a schematic block diagram showing when a supply of high-frequency power and the conductive fluid are switched using a phase as the threshold of the treatment apparatus according to the first to twelfth embodiments;

FIG. 10 is a schematic graph showing a relationship between the phase and time obtained from output voltage value information, output voltage phase information, output current value information, and output current phase information when treatment using high-frequency energy is provided to the living tissue using a treatment apparatus according to a first modification of the first to twelfth embodiments;

FIG. 12A is a schematic plan view showing the first holding member on the side nearer to the second holding member of the holding portion of the electro-surgical device of a treatment apparatus according to the second embodiment;

FIG. 12B is a schematic longitudinal sectional view showing the first holding member along a line 12B-12B shown in FIG. 12A of the holding portion of the electro-surgical device of the treatment apparatus according to the second embodiment;

FIG. 13A is a schematic plan view showing the first holding member on the side nearer to the second holding member of the holding portion of the electro-surgical device of a treatment apparatus according to the third embodiment;

FIG. 13B is a schematic longitudinal sectional view showing the first holding member along a line 13B-13B shown in FIG. 13A of the holding portion of the electro-surgical device of the treatment apparatus according to the third embodiment;

FIG. 15A is a schematic plan view showing the first holding member on the side nearer to the second holding member of the holding portion of the electro-surgical device of the treatment apparatus according to the fourth to sixth embodiments;

FIG. 15B is a schematic longitudinal sectional view showing the first holding member along a line 15B-15B shown in FIG. 15A of the holding portion of the electro-surgical device of the treatment apparatus according to the fourth to sixth embodiments;

FIG. 15C is a schematic longitudinal sectional view showing the first holding member along a line 15C-15C shown in FIG. 15A of the holding portion of the electro-surgical device of the treatment apparatus according to the fourth to sixth embodiments;

FIG. 16A is a schematic plan view showing the first holding member on the side nearer to the second holding member of the holding portion of the electro-surgical device of a treatment apparatus according to the seventh embodiment;

FIG. 16B is a schematic longitudinal sectional view showing the first holding member along a line 16B-16B shown in FIG. 16A of the holding portion of the electro-surgical device of the treatment apparatus according to the seventh embodiment;

FIG. 16C is a schematic transverse sectional view showing the first holding member along a line 16C-16C shown in FIG. 16A and FIG. 16B of the holding portion of the electro-surgical device of the treatment apparatus according to the seventh embodiment;

FIG. 17A is a schematic plan view showing the first holding member on the side nearer to the second holding member of the holding portion of the electro-surgical device of a treatment apparatus according to the eighth embodiment;

FIG. 17B is a schematic longitudinal sectional view showing the first holding member along a line 17B-17B shown in FIG. 17A of the holding portion of the electro-surgical device of the treatment apparatus according to the eighth embodiment;

FIG. 17C is a schematic transverse sectional view showing the first holding member along a line 17C-17C shown in FIG. 17A and FIG. 17B of the holding portion of the electro-surgical device of the treatment apparatus according to the eighth embodiment;

FIG. 21A is a schematic plan view showing the first holding member on the side nearer to the second holding member of the holding portion of the electro-surgical device of the treatment apparatus according to the tenth embodiment;

FIG. 21B is a schematic longitudinal sectional view showing the first holding member along a line 21B-21B shown in FIG. 21A of the holding portion of the electro-surgical device of the treatment apparatus according to the tenth embodiment;

FIG. 22A is a schematic perspective view showing the state of two enteric canals of a small intestine being anastomosed and also a schematic diagram along a line 22A-22A shown in FIG. 22B;

FIG. 22B is a schematic diagram showing the state in which ends of two enteric canals of a small intestine are sealed after anastomosing the two enteric canals;

FIG. 23 is a schematic diagram showing a treatment apparatus according to the eleventh and twelfth embodiments;

FIG. 27A is a schematic longitudinal sectional view showing the state in which the main body side holding portion and the detachable side holding portion of the electro-surgical device of the treatment apparatus according to the twelfth embodiment are separated; and FIG. 27B is a schematic diagram showing the state in which the main body side holding portion and the detachable side holding portion of the electro-surgical device of the treatment apparatus according to the twelfth embodiment are separated.

DETAILED DESCRIPTION OF THE INVENTION

Preferred embodiments of the present invention will be described below with reference to drawings.

First Embodiment

The first embodiment will be described using FIG. 1 to FIG. 7.

Here, as an energy device, a linear-type bipolar high-frequency energy device 12 to provide treatment through, for example, an abdominal wall is taken as an example to describe the first embodiment.

Figure 1:
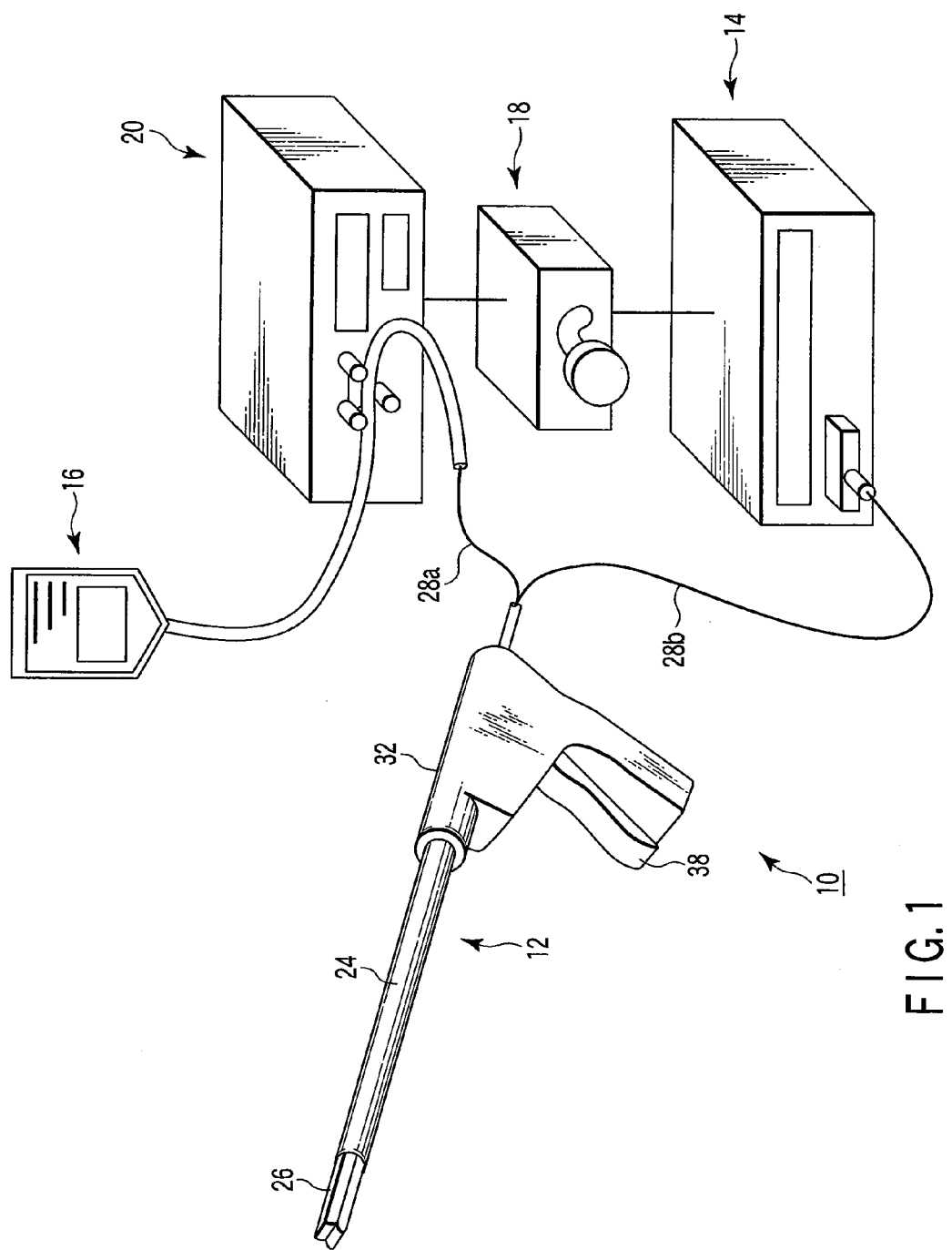
FIG. 1 is a schematic diagram showing a treatment apparatus according to first to ninth embodiments.
Figure 2:
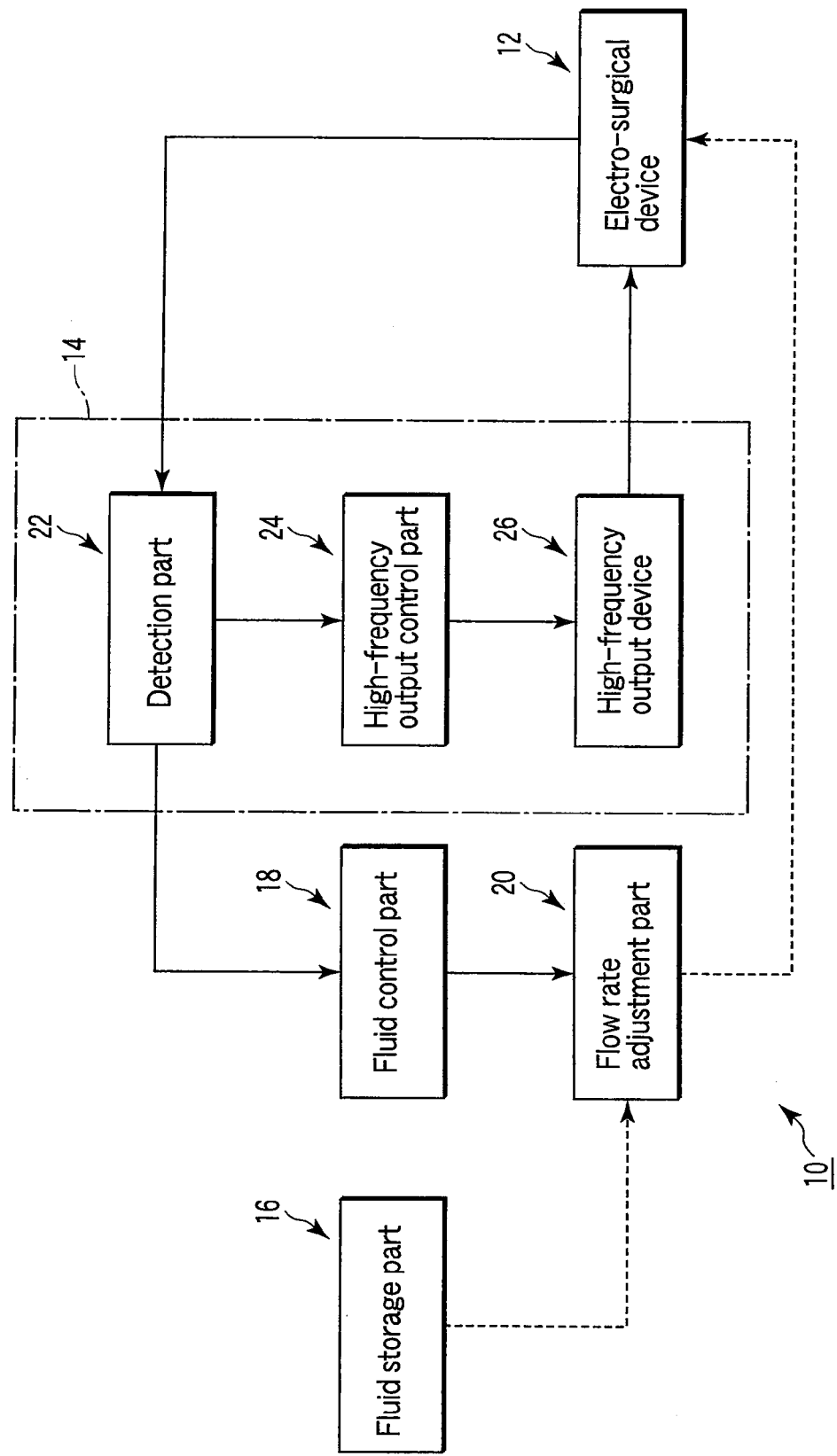
FIG. 2 is a schematic block diagram showing the treatment apparatus according to the first to ninth embodiments.

As shown in FIG. 1 and FIG. 2, a treatment apparatus 10 includes an electro-surgical device (treatment device) 12, an energy source 14 for supplying high-frequency energy to the electro-surgical device 12, a fluid storage portion 16, a fluid control portion 18, and a flow rate adjustment portion 20 to adjust the feed rate of fluid from the fluid storage portion 16.

As shown in FIG. 2, the energy source 14 includes a detection portion 22, a high-frequency output control portion 24, and a high-frequency output device 26. The detection portion 22 is connected to the electro-surgical device 12. The high-frequency output control portion 24 is connected to the detection portion 22. The high-frequency output device 26 is connected to the high-frequency output control portion 24. The high-frequency output device 26 is connected to the electro-surgical device 12.

The detection portion 22 detects electrical living information of living tissues held by a pair of holding portions 36, described later, of the electro-surgical device 12. That is, the value of current flowing through a living tissue held between the pair of holding portions 36 and the voltage value are detected and the value of impedance Z is calculated from the detected current value and voltage value to define the calculated impedance Z as living information. The high-frequency output device 26 outputs high-frequency power (high-frequency energy) based on control of the high-frequency output control portion 24. Thus, the high-frequency output control portion 24 can control output of high-frequency power from the high-frequency output device 26 to the electro-surgical device 12 based on living information detected by the detection portion 22.

A foot switch or hand switch (not shown) is connected to the energy source 14.

The energy source 14 and the flow rate adjustment portion 20 are connected to the fluid control portion 18. The fluid control portion 18 controls the flow rate adjustment portion 20. The fluid control portion 18 controls the feed rate of fluid flowing from the fluid storage portion 16 to the electro-surgical device 12, for example, by mechanically changing the inside diameter of a tube 28a by controlling to drive the flow rate adjustment portion 20. Naturally, it is also possible to reduce the feed rate of fluid to zero.

Thus, the flow rate adjustment portion 20 causes a fluid of the flow rate determined by the fluid control portion 18 to flow from the fluid storage portion 16 through a tube 28a based on living information detected by the detection portion 22 inside the energy source 14 while adjusting the flow rate thereof by the flow rate adjustment portion 20.

Thus, it is preferable to use, as a fluid (fluid body) stored in the fluid storage portion 16, a fluid that has osmosis through living tissues and can guide electric energy such as an ionized conductive fluid. For example, a physiological salt solution, hypertonic salt solution, hypotonic salt solution, and electrolyte replenisher are used as such fluids. The use of a fluid having high viscosity, for example, a gelatinized body (fluid) such as hyaluronic acid is also permitted. When a gelatinized body is used, the gelatinized body is applied to the living tissue to be treated or is penetrated so that the gelatinized body is prevented from flowing into living tissues surrounding the living tissue to be treated.

The electro-surgical device 12 includes a handle 32, a shaft 34, and a pair of holding portions 36 that can be opened and closed. The tube 28a and a cable 28b are connected to the handle 32 by being arranged together. The energy source 14 is connected to the handle 32 via the cable 28b and also the flow rate adjustment portion 20 is connected to the handle 32 via the tube 28a installed together with the cable 28b.

The handle 32 is formed in a substantially L shape. The shaft 34 is disposed at one end of the handle 32. The other end of the handle 32 is a grip portion to be held by an operator. The handle 32 has a holding portion opening/closing knob 38 disposed at the other end thereof to be arranged together. If the holding portion opening/closing knob 38 is moved closer to and away from the other end of the handle 32, a sheath 44 (See FIG. 3A and FIG. 3B), described later, moves in an axial direction thereof.

As shown in FIG. 3A and FIG. 3B, the shaft 34 includes a cylinder 42 and the sheath 44 disposed outside the cylinder 42 slidably. The cylinder 42 is fixed to the handle 32 on a base end side thereof. The sheath 44 is slidable in the axial direction of the cylinder 42.

A first recess 46a is formed outside the cylinder 42 in the axial direction thereof. In the first recess 46a, a first current-carrying line 48a connected to the energy source 14 via the cable 28b and a first duct 50a that causes a fluid stored in the fluid storage portion 16 and supplied via the tube 28a to flow toward the holding portions 36 are disposed. That is, the first duct 50a is connected to the tube 28a. The first current-carrying line 48a is connected to a first high-frequency electrode 54a, described later.

A second current-carrying line 48b connected to the energy source 14 via the cable 28b and a second duct 50b that causes a fluid stored in the fluid storage portion 16 and supplied via the tube 28a to flow toward the holding portions 36 are inserted through the cylinder 42. That is, the second duct 50b is connected to the tube 28a. The second current-carrying line 48b is connected to a second high-frequency electrode 54b, described later.

As shown in FIG. 1, FIG. 3A, and FIG. 3B, the pair of holding portions 36 are disposed at a tip of the shaft 34. As shown in FIG. 3A and FIG. 3B, one of the pair of holding portions 36 includes a first holding member (gripping member) 52a, the first high-frequency electrode (joining treatment portion) 54a as an energy releasing part, and a plurality of first openings (fluid feed portion) 56a for penetrating a fluid into a living tissue. The other of the pair of holding portions 36 includes a second holding member (gripping member) 52b, the second high-frequency electrode (joining treatment portion) 54b as an energy releasing portion, and a plurality of second openings (fluid feed portion) 56b as infusion openings for infusion of a fluid to penetrate into a living tissue.

The first holding member 52a integrally includes a first holding member main body (hereinafter, referred to mainly as a main body) 62a on which the first high-frequency electrode 54a is disposed, and a first base 64a provided on the base end side of the main body 62a.

Though a detailed structure of the second holding member 52b is not illustrated, reference numeral 62b is attached to a second holding member main body opposite to the first holding member main body 62a, and reference numeral 64b is attached to a second base opposite to the first base 64a to describe the second holding member 52b. That is, the second holding member 52b integrally includes a second holding member main body 62b, on which the second high-frequency electrode 54b is disposed, and a second base 64b provided on the base end side of the main body 62b. The side of the main body 62a of the first holding member 52a nearer to the main body 62b of the second holding member 52b and that of the main body 62b of the second holding member 52b nearer to the main body 62a of the first holding member 52a each form a holding face of a living tissue to be treated.

The base 64a of the first holding member 52a is fixed to the tip of the cylinder 42 of the shaft 34. The base 64b of the second holding member 52b, on the other hand, is supported rotatably around the tip of the cylinder 42 of the shaft 34 by a support pin 58 arranged in a direction perpendicular to the axial direction of the shaft 34. By rotating around the axis of the support pin 58, the second holding member 52b can open and close with respect to the first holding member 52a. The second holding member 52b can open and close with respect to the first holding member 52a. The second holding member 52b is energized by an elastic member 58a, such as a plate spring, so that the second holding member 52b opens with respect to the first holding member 52a.

As shown in FIG. 4A and FIG. 4B, an outer surface of the main bodies 62a and 62b of the first holding member 52a and the second holding member 52b is formed as a smooth curve. Similarly, the outer surface of the bases 64a and 64b of the first holding member 52a and the second holding member 52b is also formed as a smooth curve. When the second holding member 52b is closed with respect to the first holding member 52a, the respective transverse section of the main bodies 62a and 62b of the first holding member 52a and the second holding member 52b is formed as a substantially circular or substantially elliptical shape. When the second holding member 52b is closed with respect to the first holding member 52a, the bases 64a and 64b are formed in a cylindrical shape. In this state, diameters of the base end of the main bodies 62a and 62b of the first holding member 52a and the second holding member 52b are formed larger than those of the bases 64a and 64b of the first holding member 52a and the second holding member 52b. Moreover, a level difference 63 is formed between the main bodies 62a and 62b and the bases 64a and 64b of the first holding member 52a and the second holding member 52b respectively.

Here, when the second holding member 52b is closed with respect to the first holding member 52a, an outer circumferential surface in a substantially circular or substantially elliptical shape together with the bases 64a and 64b of the first holding member 52a and the second holding member 52b is formed flush with or slightly larger than that of the tip part of the cylinder 42. Thus, the sheath 44 can be slid with respect to the cylinder 42 to cover the bases 64a and 64b of the first holding member 52a and the second holding member 52b with a tip part thereof. In this state, as shown in FIG. 3A, the first holding member 52a and the second holding member 52b are closed against an energizing force of the elastic member 58a. If the sheath 44 is slid to the base end side of the cylinder 42 from a state in which the bases 64a and 64b of the first holding member 52a and the second holding member 52b are covered with the tip part of the sheath 44, as shown in FIG. 3B, the second holding member 52b opens with respect to the first holding member 52a with the energizing force of the elastic member 58a.

As shown in FIG. 4A and FIG. 4B, a duct arranging portion 72a to arrange the first duct 50a is formed inside the first holding member 52a. That is, the duct arranging portion 72a is formed in the first holding member main body 62a and the base 64a and the first duct 50a is disposed in the duct arranging portion 72a. The first duct 50a preferably has a quadrangular cylindrical shape, but other various shapes whose transverse section is, for example, a circular, elliptical, or polygonal shape are permitted.

The first duct 50a extends to the handle 32 along the first recess 46a on the outer circumferential surface of the cylinder 42. The first duct 50a extends as the tube 28a from the handle 32 and is disposed in the flow rate adjustment portion 20, and the like. Thus, a liquid such as a conductive fluid can be infused into the first openings 56a via the first duct 50a while adjusting the flow rate thereof. That is, the first openings 56a, the first duct 50a, the tube 28a, and the flow rate adjustment portion 20 form a fluid feed portion. The first openings 56a are disposed inside of an edge (holding face) 80a to prevent a conductive fluid from flowing out of the first holding member 52a.

In the first main body 62a, an electrode arrangement portion 74a is formed as a mount where the first high-frequency electrode 54a is arranged. The first high-frequency electrode 54a is plate-shaped, has a plurality of circular in-plane openings (through holes), and a contact surface with a living tissue on the side opposite to the second holding member 52b is formed in the plane (holding face). The first high-frequency electrode 54a is fixed to the electrode arrangement portion 74a. The plurality of openings of the first high-frequency electrode 54a are formed, for example, on the central axis of the first high-frequency electrode 54a with the same diameter at predetermined intervals.

The first high-frequency electrode 54a is electrically connected to a first electrode connector 55a through the base end, for example, on the opposite side of the side opposite to the second holding member 52b. The first electrode connector 55a is connected to the cable 28b extended from the handle 32 via the first current-carrying line 48a.

Though not shown, the main body 62b and the second high-frequency electrode 54b of the second holding member 52b are formed symmetrically with respect to the main body 62a and the first high-frequency electrode 54a of the first holding member 52a. Thus, when the second holding member 52b is closed with respect to the first holding member 52a, as shown in FIG. 3A, the first high-frequency electrode 54a of main body 62a of the first holding member 52a and the second high-frequency electrode 54b (See FIG. 3A) of main body 62b of the second holding member 52b are mutually brought into contact. Then, when energy (high-frequency power) is supplied from the energy source 14, high-frequency power is supplied to a living tissue in contact with the first high-frequency electrode 54a and the second high-frequency electrode 54b and the living tissue is heated. At this point, the first high-frequency electrode 54a and the second high-frequency electrode 54b each serve as a sensor and measure the current passing between the first high-frequency electrode 54a and the second high-frequency electrode 54b through the living tissue, the voltage and the like to input signals thereof to the detection portion 22 of the energy source 14 through the first current-carrying line 48a and the second current-carrying line 48b.

As shown in FIG. 4A and FIG. 4B, each of the plurality of openings (through holes) of the first high-frequency electrode 54a of the first holding member 52a has a first opening 56a for infusing a conductive fluid disposed therein. That is, the first duct 50a has the plurality of openings (the first openings 56a) formed by being bent in a substantially L shape inside the first holding member main body 62a.

A first fluid discharge prevention groove 76a opened as a flow channel of fluid is formed outside the electrode arrangement portion 74a. The first fluid discharge prevention groove 76a is formed annularly with concave longitudinal and transverse sections. Moreover, a first fluid discharge groove 78a opened as a flow channel of fluid is formed at the base 64a of the first holding member 52a. The first fluid discharge groove 78a has a traverse section formed in a concave shape. The surface of the first high-frequency electrode 54a is preferably positioned slightly higher than the first fluid discharge prevention groove 76a.

The edge 80a of the first holding member 52a is formed outside the first fluid discharge prevention groove 76a. Thus, the surface (hereinafter, referred to as a contact surface (holding face)) in contact with a living tissue of the edge 80a on the side of the second holding member 52b nearer to the main body 62b is formed, for example, as a flat surface.

Since the second holding member 52b is formed symmetrically with respect to the first holding member 52a, most of a description about the structure thereof is omitted here. The second duct 50b extends to the handle 32 by passing through the cylinder 42 of the shaft 34. Then, the second duct 50b extends as the tube 28a arranged together with the cable 28b from the handle 32 before being connected to the flow rate adjustment portion 20 and the like. Thus, a liquid such as a conductive fluid can be infused into the second openings 56b through the second duct 50b.

Though the first openings 56a and the second openings 56b are each formed in a circular shape in FIG. 4A, the shape is not limited to the circular shape and various shapes such as an elliptical and polygonal shape are also permitted. The arrangement of the first openings 56a in the first holding member 52a and that of the second openings 56b in the second holding member 52b are not limited to that in a single row at predetermined intervals in a longitudinal direction inside the first high-frequency electrode 54a and the second high-frequency electrode 54b, and the arrangement in a plurality of rows and that in a random fashion are also permitted.

Next, the action of the treatment apparatus 10 according to the present embodiment will be described.

As shown in FIG. 3A, when the second holding member 52b is closed with respect to the first holding member 52a, the holding portion 36 and the shaft 34 of the electro-surgical device 12 are inserted, for example, into an abdominal cavity through an abdominal wall. The holding portion 36 of the electro-surgical device 12 is brought opposite to living tissues to be joined (to be treated) by tissue welding, tissue sealing and the like.

The holding portion opening/closing knob 38 of the handle 32 is operated to hold (grip) living tissues to be joined by the first holding member 52a and the second holding member 52b. At this time, the sheath 44 is moved relative to the cylinder 42 toward the based end side of the shaft 34. The first base 64a of the first holding member 52a and the second base 64b of the second holding member 52b cannot be maintained in a cylindrical shape due to an energizing force of the elastic member 58a, and the second holding member 52b opens with respect to the first holding member 52a.

Then, the living tissues to be treated are arranged between the first high-frequency electrode 54a of the first holding member 52a and the second high-frequency electrode 54b of the second holding member 52b. In this state, the holding portion opening/closing knob 38 of the handle 32 is operated. At this time, the sheath 44 is moved relative to the cylinder 42 toward the tip part side of the shaft 34. The first base 64a of the first holding member 52a and the second base 64b of the second holding member 52b are closed to form a cylindrical shape by the sheath 44 against the energizing force of the elastic member 58a. Thus, the first holding member main body 62a integrally formed with the first base 64a of the first holding member 52a and the second holding member main body 62b integrally formed with the second base 64b of the second holding member 52b are closed. That is, the second holding member 52b is closed with respect to the first holding member 52a. In this manner, the living tissues to be joined are held between the first holding member 52a and the second holding member 52b.

At this point, the living tissues to be joined are in contact with both the first high-frequency electrode 54a of the first holding member 52a and the second high-frequency electrode 54b of the second holding member 52b. Moreover, a peripheral tissue of the living tissues to be joined are in close contact with both the edge (contact surface, holding face) 80a of the first holding member 52a and an edge (contact surface, holding face) 80b of the second holding member 52b.

In this state, the foot switch or hand switch connected to the energy source 14 is operated. Energy is supplied to the first high-frequency electrode 54a and the second high-frequency electrode 54b from the energy source 14 via the cable 28, the first current-carrying line 48a and the second current-carrying line 48b, and the first current-carrying connector 55a and a second current-carrying connector 55b respectively.

The first high-frequency electrode 54a passes a high-frequency current to the second high-frequency electrode 54b through the living tissues to be joined. Thus, the living tissues to be joined between the first high-frequency electrode 54a and the second high-frequency electrode 54b are heated. If the living tissues to be joined are heated in this manner, the living tissues are gradually dehydrated and denatured before being integrated (living tissues are welded).

A conductive fluid stored in the fluid storage portion 16 and whose flow rate is adjusted by the flow rate adjustment portion 20 controlled by the fluid control portion 18 is fed to the living tissues to be joined from the flow rate adjustment portion 20 via the tube 28a, the first duct 50a and the second duct 50b, and the first openings 56a and the second openings 56b. Here, the conductive fluid is controlled by the fluid control portion 18 connected to the energy source 14 and thus, for example, feeding of the conductive fluid can freely be set in accordance with settings of the energy source 14 such as feeding the conductive fluid together while high-frequency energy is supplied from the energy source 14 or feeding the conductive fluid while a supply of high-frequency energy is stopped, and based on the setting thereof, the conductive fluid is automatically or forcibly fed.

Here, when the first high-frequency electrode 54a is fixed to the electrode arrangement portion 74a of the first holding member 52a, the surface (holding face) of the first high-frequency electrode 54a exposed to the second holding member 52b side is positioned slightly higher than the first fluid discharge prevention groove 76a. Similarly, though not shown, when the second high-frequency electrode 54b is fixed to an electrode arrangement portion 80b of the second holding member 52b, the surface (holding face) of the second high-frequency electrode 54b exposed to the first holding member 52a side is positioned slightly higher than a second fluid discharge prevention groove 76b. Thus, fluids such as a fed liquid (conductive fluid) and a liquid and vapor originating by the living tissues to be joined being dehydrated flow into the first fluid discharge prevention groove 76a of the first holding member 52a and the second fluid discharge prevention groove 76b of the second holding member 52b. At this point, the first edge 80a and the second edge 80b each function as a contact surface (holding face) in close contact with the living tissues to be joined, and thus the edges 80a and 80b and the first and second fluid discharge prevention grooves 76a and 76b each serve to prevent a liquid from leaking out.

Consequently, a liquid originating from the living tissues and an excessively fed conductive fluid flow into the first and second fluid discharge prevention grooves 76a and 76b of the first holding member 52a and second holding member 52b respectively. Then, the liquid that has flown in this manner flows toward the first fluid discharge groove 78a and a second fluid discharge groove 78b of the bases 64a and 64b of the first holding member 52a and second holding member 52b communicatively connected to the first and second fluid discharge prevention grooves 76a and 76b. Then, as shown in FIG. 3B, the liquid is led to the outside from the first and second fluid discharge grooves 78a and 78b through the inside of the cylinder 42, through holes 42a provided in the cylinder 42, and through holes 44a provided in the sheath 44.

Figure 5:
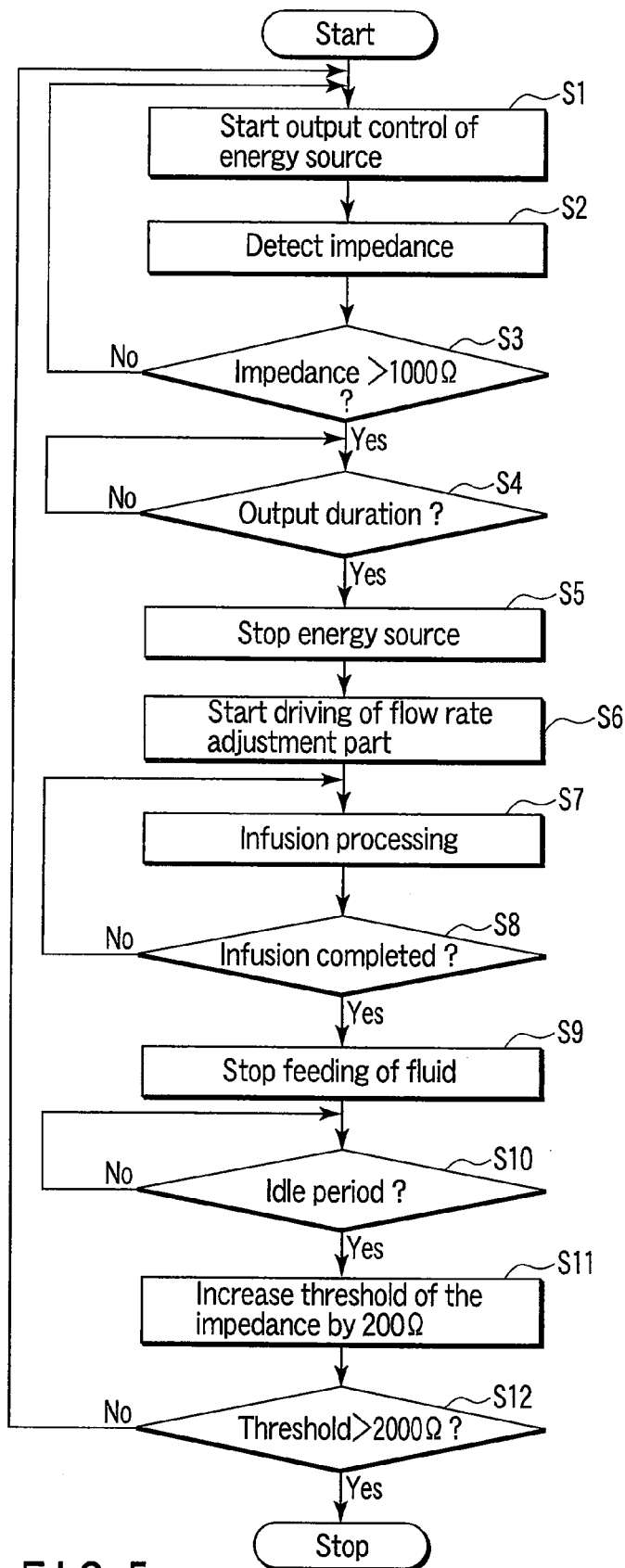
FIG. 5 is a schematic flow chart when treatment using high-frequency energy is provided to a living tissue by using the treatment apparatus according to the first to ninth and tenth to twelfth embodiments.
Figure 6:
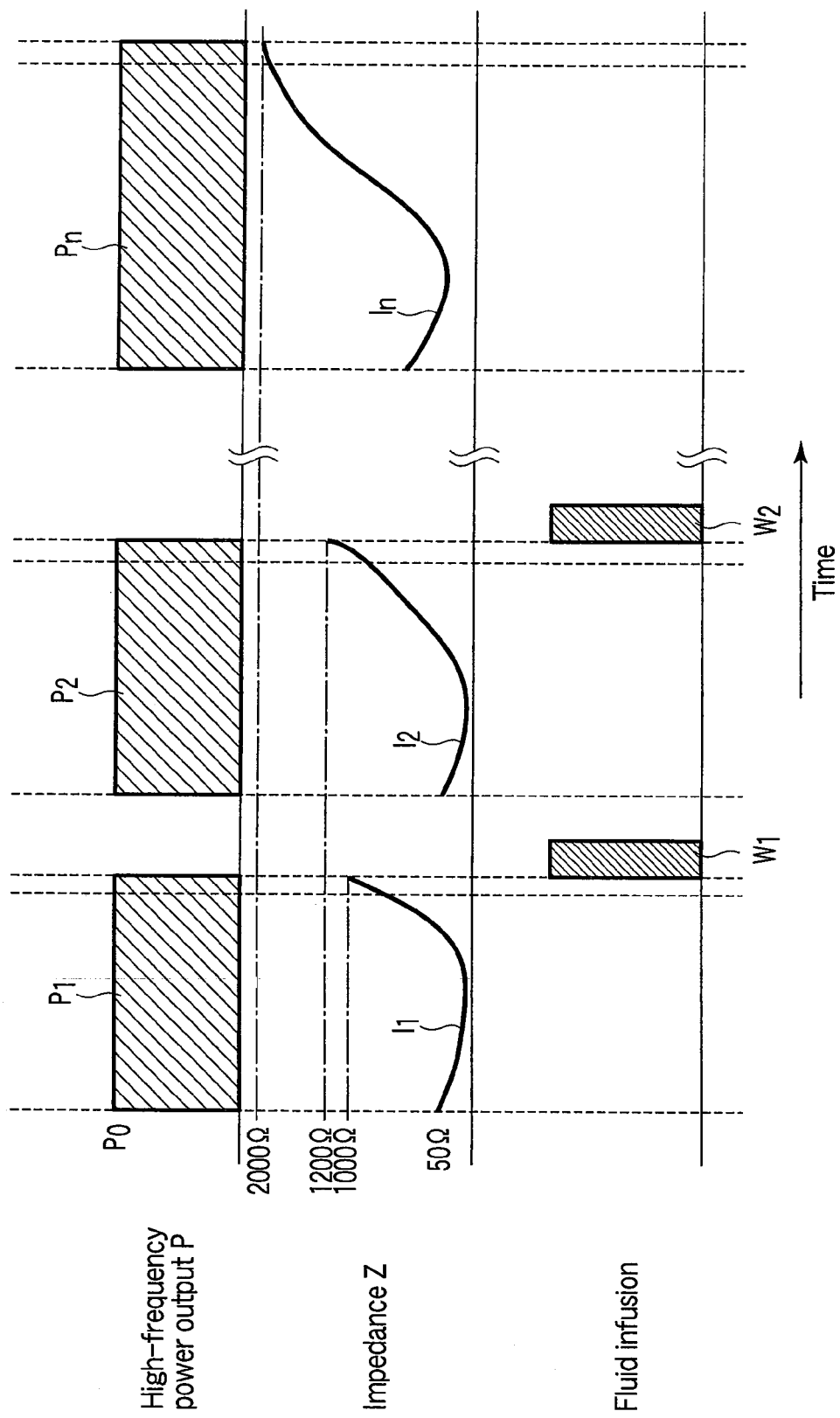
FIG. 6 is a schematic diagram exemplarily showing output of high-frequency power from an energy source, conditions (electrical information such as an impedance Z) of a living tissue to be treated, and control of a feed rate of fluid from a flow rate control portion when the living tissue is treated using the treatment apparatus according to the first to twelfth embodiments.
Figure 7:
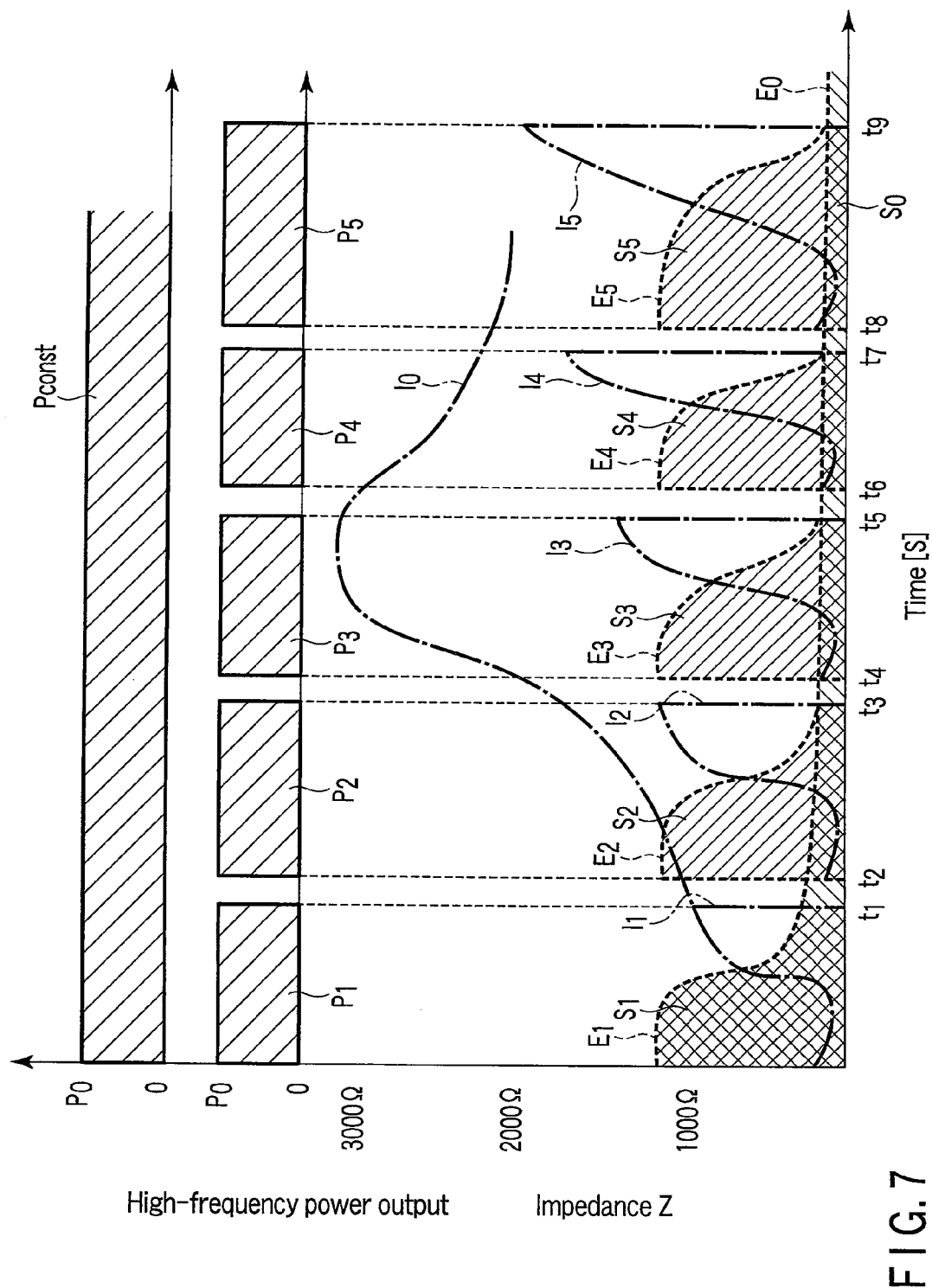
FIG. 7 is a schematic diagram showing impedance behavior with respect to high-frequency output and high-frequency electric energy applied to the living tissue to be treated when high-frequency power is continuously applied to the living tissue to be treated and also impedance behavior with respect to high-frequency output and high-frequency electric energy applied to the living tissue to be treated when the same treatment is repeated after high-frequency power is applied to the living tissue to be treated using the treatment apparatus according to the first to twelfth embodiments, and when the impedance of the living tissue reaches a predetermined threshold, the impedance of the living tissue is forced to drop by stopping application of the high-frequency power and feeding a conductive fluid to the living tissue to be treated.

Next, the control method of output of high-frequency power and infusion of a conductive fluid will be described. Here, it is assumed that the treatment apparatus 10 is programmed to operate as shown in FIG. 5. FIG. 6 shows an example of output of high-frequency power from the energy source 14, conditions (electrical information such as an impedance Z) of living tissues to be joined, and a feed rate of fluid from the flow rate adjustment portion 20 in accordance with the flow chart shown in FIG. 5. FIG. 7 shows a result of treatment according to steps described below performed on the living tissues to be joined in accordance with the flow chart shown in FIG. 5.

The operation of the treatment apparatus 10 will be described in detail below along the flow of the flow chart shown in FIG. 5.

When the foot switch or hand switch (not shown) connected to the energy source 14 is turned on by pressing the switch or the like, the energy source 14 is activated and the program shown in FIG. 5 is executed.

The energy source 14 is driven while controlling the high-frequency output device 26 inside thereof through the high-frequency output control portion 24 to output high-frequency power (high-frequency energy) from the high-frequency output device 26 (step S1). Here, as shown in FIG. 6, it is assumed that high-frequency power $P_0$ of fixed output is output. That is, high-frequency power is supplied to a portion of living tissues held between the first and second holding bodies 52a and 52b in contact with the electrodes 54a and 54b. That is, high-frequency energy is provided to the living tissues held between the electrodes 54a and 54b. Thus, the living tissues in contact with the electrodes 54a and 54b are heated. That is, Joule heat is generated in the living tissues held between the electrodes 54a and 54b to heat the living tissues themselves. Cell membranes of the living tissues held between the electrodes 54a and 54b are destroyed by an action of high-frequency power and materials inside cell membranes are discharged before being made uniform with components outside cells such as collagen. Therefore, when high-frequency power is provided between the electrodes 54a and 54b, the inside of the living tissues are denatured (the living tissues are cauterized) while the living tissues themselves are heated and dehydrated.

Next, the impedance Z of the living tissues held by the first and second holding bodies 52a and 52b and in contact with the high-frequency electrodes 54a and 54b is detected by the detection portion 22 inside the energy source 14 (step S2). That is, the high-frequency electrodes 54a and 54b of the electro-surgical device 12 transmit signals based on living information of the living tissues to be joined in contact with the high-frequency electrodes 54a and 54b to the detection portion 22 of the energy source 14 through the first and second current-carrying lines 48a and 48b. Thus, the impedance Z of the living tissues held between the high-frequency electrodes 54a and 54b is measured by the detection portion (collection means for collecting living information) 22 through the high-frequency electrodes 54a and 54b. Thus, the detection portion 22 calculates the value (living information) of the impedance Z based on the transmitted signals. The impedance Z (initial value) when treatment is started changes depending on the size and shape of the electrode and, as shown in FIG. 6 and FIG. 7, is about 50 [Ω], for example. Then, with the living tissues increasingly cauterized by high-frequency power being applied to the living tissues, the value of impedance Z once drops from about 50 [Ω] and then increases. Such an increase in the value of impedance Z indicates that moisture in the living tissues is being lost and drying is in progress.

Next, whether the calculated impedance Z exceeds, for example, 1000Ω (not limited to this value and any other value can be set) set as a threshold to the high-frequency output control portion 24 is determined (step S3).

If it is determined at step S3 that the impedance Z does not exceed the threshold 1000Ω, processing returns to step S1 to repeat step S1 and subsequent steps. On the other hand, if it is determined at step S3 that the impedance Z exceeds the threshold 1000Ω, output is continued for a preset output duration (step S4). The output duration may be set at zero. In the present embodiment, the output duration is set at zero.

When it is determined at step S4 that output continued for the preset output duration, the high-frequency output control portion 24 stops output of high-frequency power from the high-frequency output device 26 (step S5).

Next, the high-frequency output control portion 24 transmits a signal to the fluid control portion 18 to drive the flow rate adjustment portion 20 (step S6).

Thus, an appropriate amount of fluid is infused from the first openings 56a through the tube 28a and the first duct 50a inside the electro-surgical device 12 while being adjusted by the flow rate adjustment portion 20 and also an appropriate amount $W_1$ of fluid is infused from the second openings 56b through the tube 28a and the second duct 50b inside the electro-surgical device 12 (step S7). Thus, a conductive fluid is infused toward the living tissues to be joined whose treatment (dehydration) is in an advanced stage. Then, the infused fluid penetrates into the living tissues to be joined whose dehydration is in an advanced stage. By causing a fluid to penetrate into the living tissues to be joined, as described above, the value of impedance Z is forced to go down. At this point, since the first and second fluid discharge prevention grooves 76a and 76b are formed, a conductive fluid that does not penetrate into the living tissues can be prevented from flowing out of the holding portions 36. Thus, when a sequence of similar processing is performed later by setting the threshold higher, peripheral tissues of the living tissues to be joined can be prevented from being heated as well.

Subsequently, at step S7, whether a preset amount of fluid has been fed (step S8) is determined.

If it is determined that the preset amount $W_1$ of fluid has been fed, the fluid control portion 18 controls the flow rate adjustment portion 20 to set the flow rate of feeding to zero to end infusion of the fluid (step S9).

Next, after stopping the feeding of the conductive fluid passing through the tube 28a by driving the flow rate adjustment portion 20 at step S9, whether a preset idle period has passed (step S10) is determined. The idle period may be zero, that is, high-frequency output may be continuous. In the present embodiment, the idle period of several seconds, for example, one second is inserted.

If it is determined at step S10 that the idle period has passed, as shown in FIG. 6, the setting of the threshold 1000Ω of the impedance Z is increased by 200Ω each time (step S11).

At this point, for example, the threshold 2000Ω (not limited to this value and any value can be set), which is preset as a termination condition, and the current threshold are compared (step S12). If the current threshold is smaller than the threshold 2000Ω of the termination condition, processing returns to step S1 to re-execute step S1 and subsequent steps described above.

At this point, the threshold is 1200Ω and thus, step S1 and subsequent steps are re-executed after returning to step S1.

The initial value of impedance Z detected by the detection portion 22 is about 50Ω. That is, the impedance Z is not the final impedance Z of 1000Ω after high-frequency power is previously supplied, but is one forced to go down by infusion of a conductive fluid into the living tissues to be joined.

If the threshold becomes larger than the termination condition of 2000Ω at step S12 while repeating step S1 to S12, output is automatically stopped (step S13).

In addition to determining whether the threshold exceeds a threshold set as a termination condition, other termination conditions may be set, such as terminating after repeating the flow chart shown in FIG. 5 as many times as the number set to the high-frequency output control portion 24.

In the present embodiment, not only flushing a preset amount at a time, but also settings of flushing several times and flowing an infusion amount per unit time for some time are permitted as infusion of the conductive fluid.

A sequence of the control method as shown in FIG. 5 is performed when the foot switch or hand switch connected to the energy source 14 is continuously pressed down. If, on the other hand, the foot switch or hand switch is released after being pressed down, treatment of the living tissues is forced to terminate. Naturally, when it is determined that the threshold exceeds 2000Ω, treatment terminates automatically. At this point, it is preferable to notify the user of the electro-surgical device 12 that treatment has terminated by a buzzer, light, display to that effect, or the like. It is also preferable to change the tone of buzzer how treatment is terminated.

If, in contrast to the above steps, living tissues held by the holding portions 36 are treated by continuously outputting high-frequency power of output $P_0$ as shown by a symbol $P_{const.}$ in FIG. 7, as shown by a symbol $I_0$, the measured impedance Z generally increases, for example, to a level exceeding 3000Ω with the passage of time, and then gradually drops. However, as shown by a symbol $E_0$, high-frequency electric energy that can actually be caused to act on the living tissues continues to drop with an increase in the impedance Z shown by the symbol $I_0$ and still continues to drop regardless of a drop of the impedance Z after increasing to about 3000Ω. Whether the living tissues are treated is determined not by the impedance Z shown by the symbol $I_0$, but an area $S_0$ below the high-frequency electric energy shown by the symbol $E_0$. Thus, an increase in high-frequency electric energy with respect to the initial state is small. That is, the impedance Z of the held living tissues increases to a level exceeding about 3000Ω with the passage of time and it becomes difficult to supply high-frequency energy to the living tissues to be joined. Thus, it may become necessary to treat the living tissues longer to reach a desired state or treatment may not go far enough to reach a desired state.

On the other hand, like the above steps of the control method, the supply of high-frequency power of output $P_0$ is stopped when the measured impedance Z reaches the threshold of 1000Ω and then, the value of impedance Z is forced to drop by causing a physiological salt solution as a conductive fluid to penetrate by infusing the physiological salt solution into living tissues. Subsequently, when high-frequency power of the same output $P_0$ is supplied until the impedance Z reaches 1200Ω, the locus of the impedance Z is substantially the same as that when the threshold is 1000Ω and an increase in high-frequency electric energy with respect to the initial state shown by a symbol $E_1$ maintains substantially the same state. Thus, high-frequency electric energy that can actually be caused to act on the living tissues maintains a substantially fixed state. That is, energy is transferred to the living tissues.

Subsequently, by infusing a conductive fluid toward the living tissues to be joined for penetration into the living tissues while the threshold is changed to increase, for example, by 200Ω, such as 1400Ω, 1600Ω, 1800Ω, and 2000Ω, a large amount of high-frequency electric energy can be provided to the living tissues each time high-frequency power is output.

Therefore, by infusing a conductive fluid for penetration into the living tissues to be joined while high-frequency power is stopped after being output and then, high-frequency power is output again, according to the present embodiment, more high-frequency electric energy than when the high-frequency power $P_{const.}$ that is always constant is output can be caused to act on the living tissues. As shown in FIG. 7, when areas $S_1$, $S_2$, $S_3$, $S_4$, and $S_5$ below high-frequency electric energy $E_1$, $E_2$, $E_3$, $E_4$, and $E_5$ between a time when high-frequency electric energy becomes zero each time the threshold is reached and a time when, after a new threshold is set, the new threshold is reached are added, the added value is sufficiently greater than the area $S_0$ below the continuous high-frequency electric energy $E_0$.

Thus, for example, when living tissues are joined together, a greater effect can be achieved. That is, by infusing a conductive fluid for penetration into the living tissues to be joined (to be welded, to be sealed) after providing treatment by high-frequency power with the threshold of the impedance Z of 1000Ω, treatment of the living tissues can be advanced (a joining force between living tissues (tissue welding force, tissue sealing force) increases gradually) even when treatment with the threshold of 1200Ω is provided.

Thus, in the present embodiment, control to provide treatment (joining of living tissues) until the threshold reaches 2000Ω has been described above, but when the added value of areas $S_1$, $S_2$, ... $S_n$ below high-frequency electric energy $E_1$, $E_2$, ... $E_n$ reaches a predetermined value (a threshold different from the above thresholds), treatment may be terminated by stopping the supply of high-frequency energy from the energy source 14. This is because the added value of areas $S_1$, $S_2$, ... $S_n$ represents an integrated value of high-frequency electric energy $E_1$, $E_2$, ... $E_n$ applied to the living tissues to be joined (to be treated). Using such method of control, treatment can be terminated depending on the high-frequency electric energy applied to the living tissues regardless of whether the threshold of the impedance Z reaches 2000Ω.

Here, an example of joining living tissues is taken to describe the present embodiment, but it is also possible to simply coagulate living tissues.

According to the present embodiment, as described above, the effects below can be achieved.

When a high-frequency current (high-frequency energy) is provided to living tissues to be joined (to be welded, to be sealed) held between the high-frequency electrodes 54a and 54b of the first and second holding bodies 52a and 52b from the energy source 14, a conductive fluid can be fed to the living tissues to be joined. Moreover, the fluid such as the conductive fluid and vapor and the like originating from the living tissues can be prevented from flowing to peripheral living tissues from the living tissues to be joined by the first and second fluid discharge prevention grooves 76a and 76b, and can be led to the outside through the first and second fluid discharge grooves 78a and 78b.

So, an increase in impedance Z can be inhibited solely in the living tissues to be joined held between the high-frequency electrodes 54a and 54b of the first and second holding bodies 52a and 52b, so that high-frequency energy can be effectively supplied to promote protein denaturation of the living tissues to be joined. Thus, for example, when living tissues are joined together, a stronger joining force (tissue welding force, tissue sealing force) can be obtained. Moreover, a thermal effect can more reliably be prevented from spreading to peripheral tissues from living tissues to be joined to which high-frequency power is supplied when the living tissues are treated while a conductive fluid is fed, which is superior also in terms of healing of the living tissues after treatment.

That is, the electro-surgical device 12 producing superior operation effects that are not known in conventional technology such as providing the first and second fluid discharge prevention grooves 76a and 76b so that a conductive fluid should not flow into peripheral living tissues excluding living tissues to be joined, preventing heat damage to peripheral living tissues not to be denatured around the living tissues to be joined, further lowering the impedance Z of solely the living tissues to be joined (to be welded, to be sealed) effectively so that more high-frequency energy can be supplied.

Therefore, according to the treatment apparatus 10, electric characteristics of living tissues near the holding portions 36 of the electro-surgical device 12 can be corrected by feeding a conductive fluid so that high-frequency energy can be supplied effectively to promote protein denaturation of the living tissues near a joining surface.

In the foregoing, the treatment apparatus 10 in the present embodiment has been described using FIG. 1 to FIG. 7. However, the present embodiment is not limited to the above examples and the configuration of each part can be replaced by one having an equivalent function.

Figure 8A:
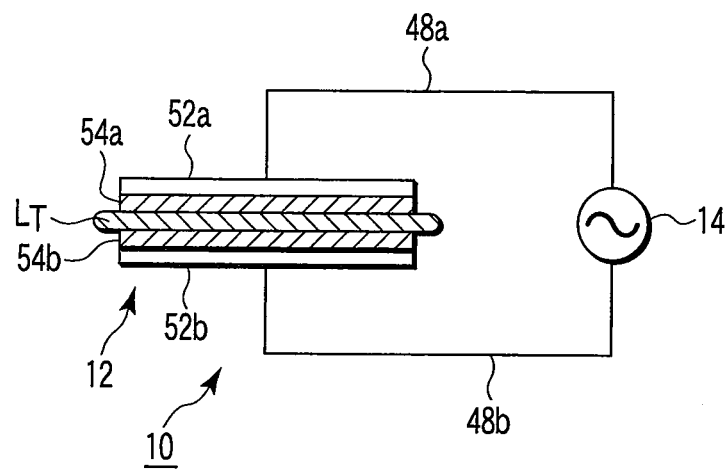
FIG. 8A is a schematic diagram when the living tissue is treated by providing bipolar high-frequency energy from the electro-surgical device of the treatment apparatus according to the first to twelfth embodiments.
Figure 8B:
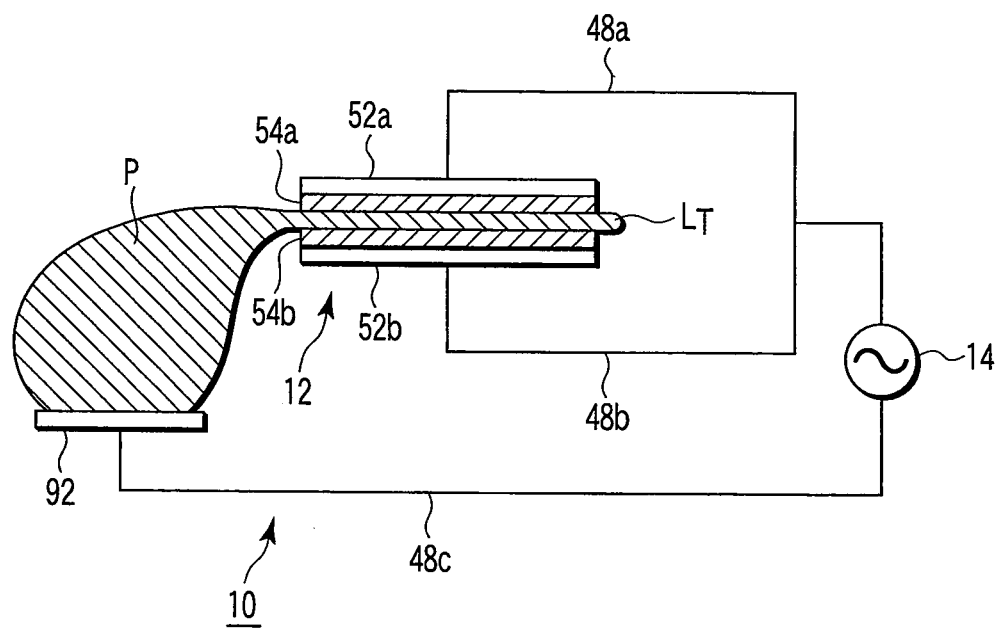
FIG. 8B is a schematic diagram when the living tissue is treated by providing monopolar high-frequency energy from the electro-surgical device of the treatment apparatus according to the first to twelfth embodiments.

Here, as shown in FIG. 8A, the use of the surgical treatment device (electro-surgical device) 12 providing bipolar high-frequency energy treatment having the electrodes 54a and 54b having different potentials in the holding bodies 52a and 52b respectively has been described, but as shown in FIG. 8B, using the surgical treatment device 12 providing a monopolar high-frequency energy treatment is also preferred. In this case, a patient P to be treated is furnished with a return electrode plate 92. The return electrode plate 92 is connected to the energy source 14 via a current-carrying line 48c. Further, the electrode 54a disposed in the first holding member 52a and the electrode 54b disposed in the second holding member 52b are at the same potential with the electrically connected first and second current supply lines 48a and 48b. In this case, an area of living tissues $L_T$ in contact with each of the first and second high-frequency electrodes 54a and 54b is small and thus, the current density is high, but that of the return electrode plate 92 becomes low. Thus, while the living tissues $L_T$ held by the holding bodies 52a and 52b are heated, heating of the living tissues $L_T$ in contact with the return electrode plate 92 is negligibly small. Therefore, only the living tissues $L_T$ held by the holding bodies 52a and 52b that are in contact with the electrodes 54a and 54b are heated and denatured.

Though not shown, when a monopolar surgical treatment device is used, a high-frequency electrode disposed only on one of the holding bodies 52a and 52b is also preferred.

In the present embodiment, conditions (state) of living tissues are detected in terms of the impedance Z at step S2 described above, but living information is not limited to the impedance Z. For example, other electrical information such as electric energy and the phase is also permitted. That is, living information includes, for example, the current, voltage and power to calculate the impedance Z, the impedance Z to be calculated, and phase information.

When treatment using high-frequency energy is provided by determining variations in phase (phase difference Δθ), the detection portion 22 shown in FIG. 2 can detect not only the voltage and current, but also the phase. Thus, when treatment using high-frequency energy is provided by determining variations in phase (phase difference Δθ), the detection portion 22 shown in FIG. 2 includes, as shown in FIG. 9, a voltage detection portion 102, a current detection portion 104, and a phase detection portion 106.

When a high-frequency voltage is generated through the high-frequency output device 26, a high-frequency current having a predetermined frequency and peak value is output to the electro-surgical device 12 via the current detection portion 104. The voltage detection portion 102 detects the peak value of the high-frequency voltage and outputs the detected peak value to the phase detection portion 106 as output voltage value information. The current detection portion 104 detects the peak value of the high-frequency current and outputs the detected peak value to the phase detection portion 106 as output current value information.

The phase detection portion 106 detects the phase of the high-frequency voltage output through the high-frequency output device 26 based on output voltage value information output from the voltage detection portion 102 and then outputs the detected phase as output voltage phase information to the high-frequency output control portion 24 together with the output voltage value information. The phase detection portion 106 also detects the phase of the high-frequency current output through the high-frequency output device 26 based on output current value information output from the current detection portion 104 and then outputs the detected phase as output current phase information to the high-frequency output control portion 24 together with the output current value information.

The high-frequency output control portion 24 calculates a phase difference $\Delta\theta$ between the high-frequency voltage and high-frequency current output through the high-frequency output device 26 based on the output voltage value information, output voltage phase information, output current value information, and output current phase information output from the phase detection portion 106.

The high-frequency output control portion 24 controls the high-frequency output device 26 to change the output state of the high-frequency current and high-frequency voltage to the ON state or OFF state based on an instruction signal output in accordance with an operation of the foot switch or hand switch and the calculated phase difference $\Delta\theta$.

As shown in FIG. 10, the phase difference $\Delta\theta$ between the high-frequency current and high-frequency voltage output through the high-frequency output device 26 is 0° or substantially 0° in an initial stage of treatment of the living tissues $L_T$. Incidentally, the threshold of the phase difference $\Delta\theta$ of the high-frequency output control portion 24 is set to 90° or a value close to 90°.

If the foot switch or hand switch is continuously pressed down and treatment of the living tissues $L_T$ held between the electrodes 54a and 54b of the pair of holding portions 36 advances, the living tissues $L_T$ are dehydrated and denatured. As the treatment advances, the phase difference $\Delta\theta$ between the high-frequency voltage and high-frequency current output through the high-frequency output device 26 increases from the state of 0° or substantially 0°, for example, after an appropriate time $t_1$.

If, subsequently, treatment of the desired region further advances with the pedal of the foot switch continuously pressed down, the phase difference $\Delta\theta$ value calculated by the high-frequency output control portion 24 takes a constant value near 90° shown in FIG. 10, for example, after time $t_2$. At this point, a conductive fluid is fed to force the value of the initial impedance value when high-frequency energy is given to the same living tissues to be joined (to be welded, to be sealed) to go down. Thus, desired treatment can be provided efficiently in a short time by using the phase difference $\Delta\theta$ (phase information), instead of the impedance Z, as described above.

In this modification, the output control portion 24 need not necessarily perform the control only when the phase difference $\Delta\theta$ is detected to take a constant value near 90° and the control may be performed when, for example, the phase difference $\Delta\theta$ takes a predetermined constant value greater than 45° and equal to or smaller than 90°.

The energy to be invested in the living tissues $L_T$ may be switched by combining both the change in impedance Z and that in phase. That is, it is preferable to appropriately set and use the earlier or later of the change in impedance Z and that in phase to reach the threshold.

In modifications and embodiments shown below, switching of the supply of high-frequency energy and a conductive fluid use mainly the impedance Z, but the phase difference $\Delta\theta$ may also be used to switch the supply of high-frequency energy and a conductive fluid.

Figure 11:
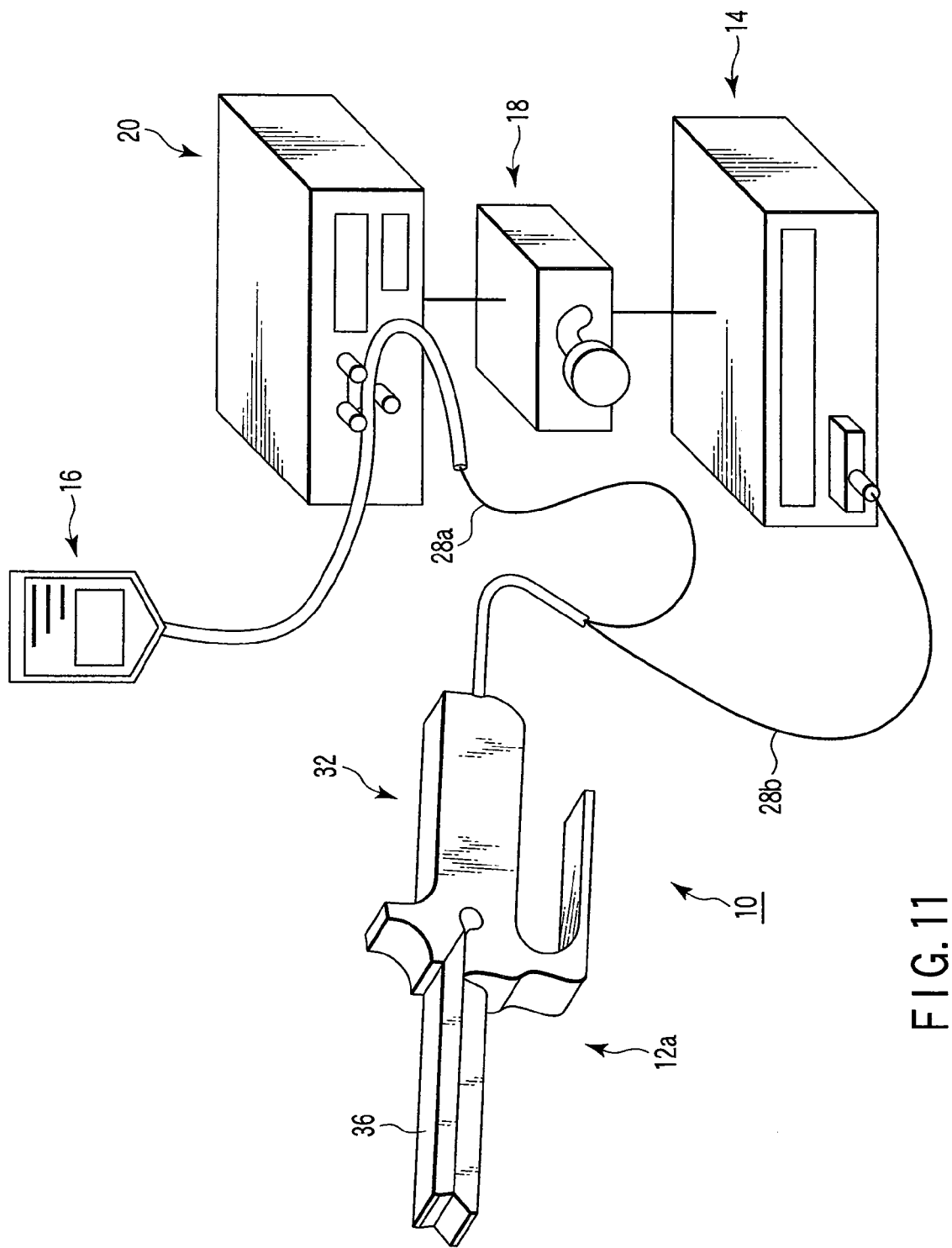
FIG. 11 is a schematic diagram showing a modification of the electro-surgical device of the treatment apparatus according to the first to ninth embodiments shown in FIG. 1.

The present embodiment has been described by taking the linear-type electro-surgical device 12 to treat living tissues in an abdominal cavity (in the body) through an abdominal wall as an example, but as shown, for example, in FIG. 11, an open linear-type electro-surgical device (treatment device) 12a to treat tissues to be joined by taking such tissues out of the body through the abdominal wall may also be used.

The electro-surgical device 12a includes the handle 32 and the holding portions 36. That is, in contrast to the electro-surgical device 12 for treatment through the abdominal wall, the shaft 34 (See FIG. 1) is removed from the electro-surgical device 12a. A member having the same operation as the shaft 34 is disposed in the handle 32. Thus, the electro-surgical device 12a can be used in the same manner as the electro-surgical device 12 shown in FIG. 1.

In the present embodiment, a conductive fluid is fed to lower the impedance Z, but together with the conductive fluid, medical fluids needed for treatment of living tissues and the like may be fed by arranging a duct, tube or the like together. Or, the tube 28a, the first and second ducts 50a and 50b, and the first and second openings 56a and 56b may suitably be used as a feed channel of not only the conductive fluid, but also medical fluids.

Second Embodiment

Next, the second embodiment will be described using FIG. 12A and FIG. 12B. The present embodiment is a modification of the first embodiment and the same reference numerals are attached to the same members described in the first embodiment and a detailed description thereof is omitted here.

As shown in FIG. 8A, the first fluid discharge prevention groove 76a (See FIG. 4A and FIG. 4B) is removed from inside the edge 80a of the main body 62a of the first holding member 52a. Then, a barrier portion (dam) 116a is formed inside the edge 80a of the main body 62a of the first holding member 52a in place of the first fluid discharge prevention groove 76a.

As shown in FIG. 12A and FIG. 12B, a level difference is formed between the surface of the first high-frequency electrode 54a and a contact surface of the barrier portion (dam) 116a. Therefore, the contact surface (holding face for living tissues) of the first barrier portion (dam) 116a is positioned higher (closer to the second high-frequency electrode 54b) than the surface of the first high-frequency electrode 54a.

Though not shown, the main body 62b and the second high-frequency electrode 54b of the second holding member 52b are also formed symmetrically with respect to the main body 62a and the first high-frequency electrode 54a of the first holding member 52a. Thus, when the second holding member 52b is closed with respect to the first holding member 52a, the barrier portion (dam) 116a of the first holding member 52a and a barrier portion (dam) 116b of the second holding member 52b are mutually brought into contact, but a space is formed between the first high-frequency electrode 54a and the second high-frequency electrode 54b.

Thus, a fluid such as an excessively fed liquid and a liquid originating from living tissues hits the inner surface of the barrier portion (dam) 116a of the first holding member 52a and that of the barrier portion (dam) 116b of the second holding member 52b. At this point, the contact surfaces of the first and second barrier portions (dams) 116a and 116b are in close contact with living tissues to be joined (to be welded, to be sealed) and thus, the inner surfaces of the barrier portions (dams) 116a and 116b each serve as a barrier to prevent a fluid such as a liquid and high-temperature vapor originating from living tissues from leaking out.

The second embodiment is a modification of the first embodiment obtained by forming the barrier portions (dams) 116a and 116b in place of the fluid discharge prevention grooves 76a and 76b of the first and second holding bodies 52a and 52b, and other components remain unchanged, thus a detailed description of operations and effects is omitted here.

Third Embodiment

Next, the third embodiment will be described using FIG. 13A and FIG. 13B. The present embodiment is a modification of the second embodiment and the same reference numerals are attached to the same members described in the second embodiment, and a detailed description thereof is omitted here.

As shown in FIG. 13B, a recess 117 is formed inside the barrier portion (dam) 116a formed in the edge 80a of the main body 62a of the first holding member 52a. In the recess 117, a plurality of first fluid discharge holes 118a passing through the first holding member 52a is formed. These first fluid discharge holes 118a are formed at predetermined intervals in the longitudinal direction of the first holding member 52a. Though not shown, the second holding member 52b is also formed symmetrically with respect to the first holding member 52a.

As shown in FIG. 13A and FIG. 13B, a level difference is formed between the surface of the first high-frequency electrode 54a and the contact surface of the barrier portion (dam) 116a, and therefore a conductive fluid and a fluid such as vapor and a liquid originating by living tissues being dehydrated can be prevented from leaking out. A fluid prevented from leaking out is led to the first fluid discharge holes 118a so that an excessive liquid can be discharged from the neighborhood of living tissues to be joined.

Next, operations of the treatment apparatus 10 according to the present embodiment will be described.

Basically, operations are the same as those of the first and second embodiments and changes include the formation of the first and second fluid discharge holes 118a and 118b inside the barrier portions (dams) 116a and 116b of the main bodies 62a and 62b of the first and second holding bodies 52a and 52b.

Thus, a fed conductive fluid and a liquid originating from living tissues to be joined are prevented, by the barrier portions (dams) 116a and 116b of the first and second holding bodies 52a and 52b, from leaking out of the holding bodies 52a and 52b.

Moreover, a liquid prevented from leaking out can be led to the first and second fluid discharge holes 118a and 118b so that an excessive liquid can be discharged from the neighborhood of living tissues to be joined.

By limiting the range of energy treatment to within each of the barrier portions (dams) 116a and 116b and discharging an excessive liquid in this manner, a contribution can be made to faster treatment.

Fourth Embodiment

Next, the fourth embodiment will be described using FIG. 14 to FIG. 15C. The present embodiment is a modification of the second embodiment and the same reference numerals are attached to the same members described in the second embodiment and a detailed description thereof is omitted here.

Figure 14:
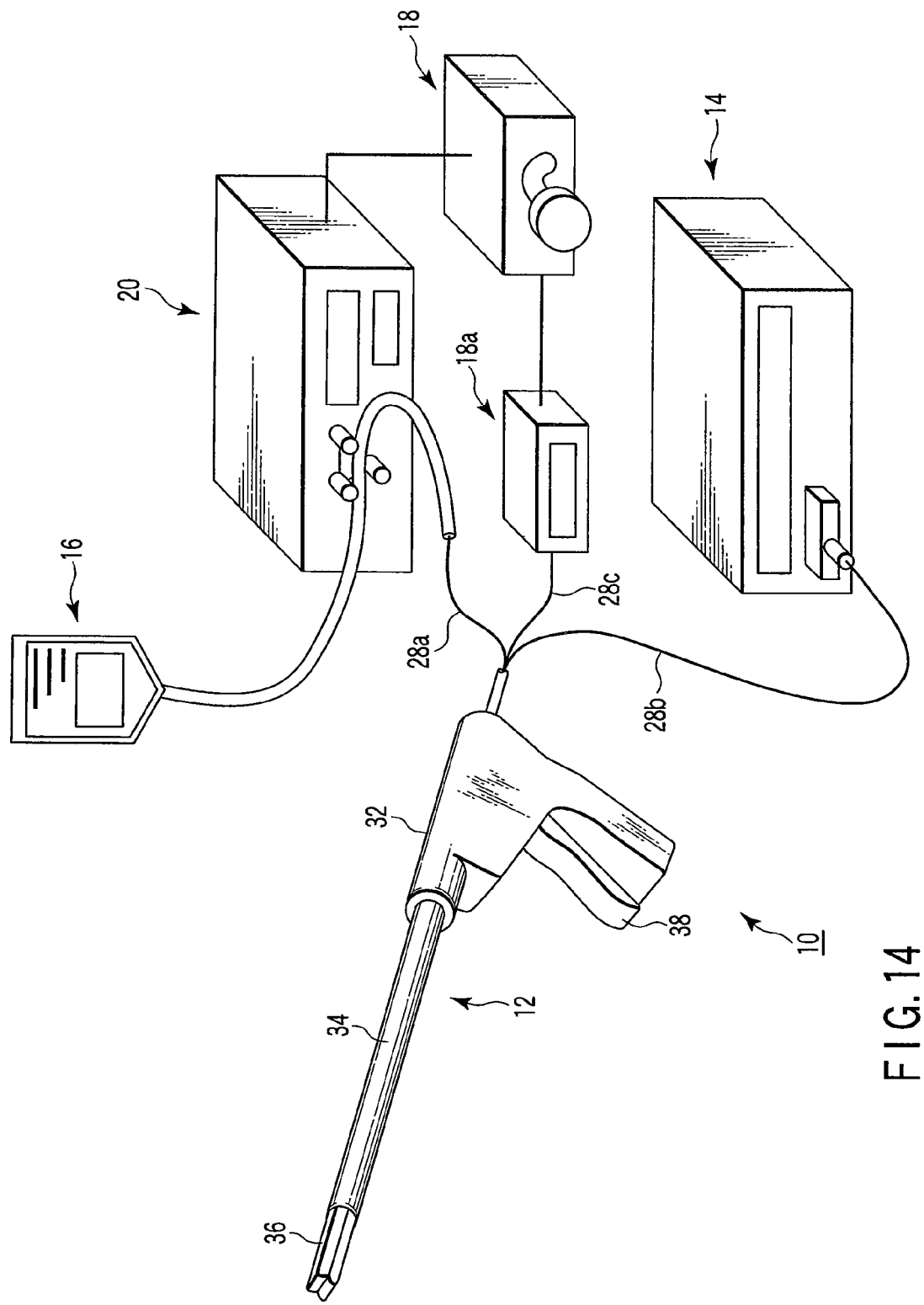
FIG. 14 is a schematic diagram showing a treatment apparatus according to the fourth to sixth embodiments.

As shown in FIG. 14, the treatment apparatus 10 includes, in addition to the electro-surgical device (treatment device) 12, the energy source 14, the storage portion 16, the fluid control portion 18, and the flow rate adjustment portion 20, a temperature measuring portion 18a connected to the handle 32 via a cable 28c. That is, when compared with the treatment apparatus 10 described in the first embodiment (See FIG. 1), the treatment apparatus 10 according to the present embodiment additionally has the temperature measuring portion 18a.

As shown in FIG. 15A and FIG. 15B, temperature sensors 120 are disposed in the electrodes 54a and 54b of the holding portions 36 of the electro-surgical device 12. As shown in FIG. 15A, these temperature sensors 120 are disposed in substantially central positions of the high-frequency electrode 54a of the main body 62a of the first holding member 52a and (though not shown) the high-frequency electrode 54b of the main body 62b of the second holding member 52b. With the temperature sensors 120 disposed in substantially central positions of the high-frequency electrodes 54a and 54b, the temperature of living tissues that can measure the highest temperature due to treatment using the high-frequency electrodes 54a and 54b can be measured.

The temperature sensor 120 is not limited to a thermocouple or a fiber thermometer and any temperature sensor with a similar function can substitute.

On the other hand, as shown in FIG. 15A and FIG. 15C, the first openings 56a are formed symmetrically with respect to the central axis of the first holding member 52a at a position shifted by a predetermined distance from the central axis thereof. A conductive fluid can be infused into living tissues by these first openings 56a. While the number of the first openings 56a is larger than that of the openings 56a described in the first embodiment (See FIG. 4A and FIG. 4B), the opening area of each of the first openings 56a is smaller, so that control of the flow rate adjustment portion 20 by the fluid control portion 18 remains unchanged.

Accordingly, in addition to the impedance Z detected by the detection portion 22 of the energy source 14 described in the first embodiment, the temperature of living tissues to be joined can correctly be measured by the temperature sensor 120 and the temperature measuring portion 18a. Thus, the flow rate adjustment portion 20 can be controlled by the fluid control portion 18 depending on the measured temperature.

Next, operations of the treatment apparatus 10 according to the present embodiment will be described.

Energy is supplied to each of the first high-frequency electrode 54a and the second high-frequency electrode 54b from the energy source 14 to heat and denature living tissues between the first high-frequency electrode 54a and the second high-frequency electrode 54b.

At this point, if the temperature of the living tissues to be joined rises excessively (for example, the temperature of 100° C. or higher is measured), the impedance Z of the living tissues held between the electrodes 54a and 54b rises. Thus, it becomes difficult to proceed with treatment even if high-frequency energy is provided to the living tissues to be joined. Thus, the temperature of the living tissues to be joined (to be welded, to be sealed) is measured by the temperature sensor 120 and the temperature measuring portion 18a and a suitable conductive fluid in accordance with the temperature is fed from the openings 56a. The temperature of the living tissues is forced to go down (the impedance Z is lowered) to facilitate the supply of high-frequency energy.

According to the present embodiment, as described above, effects below can be achieved.

When high-frequency power is applied to living tissues to be joined held by the first and second holding bodies 52a and 52b, a conductive fluid can be fed in accordance with, in addition to the impedance Z, the state (temperature) of the living tissues to be joined (to be welded, to be sealed) by the treatment apparatus 10.

So, an increase in impedance Z can be inhibited solely in the living tissues to be joined held (gripped) between the electrodes (holding faces) 54a and 54b so that high-frequency energy can be effectively supplied to promote protein denaturation on the joining surface. Thus, for example, when living tissues are attempted to be joined together, a stronger joining force (tissue welding force, tissue sealing force) can be obtained.

Fifth Embodiment

Next, the fifth embodiment will be described. The present embodiment is a modification of the fourth embodiment and the same reference numerals are attached to the same members described in the fourth embodiment and a detailed description thereof is omitted here.

The treatment apparatus 10 in the fifth embodiment is obtained by replacing the temperature sensor 120 described in the fourth embodiment by a pressure sensor (reference numeral 120 is attached for convenience) and the temperature measuring portion 18a by a pressure measuring portion (reference numeral 18a is attached for convenience). Thus, the fifth embodiment will be described using FIG. 14 to FIG. 15C used for the fourth embodiment.

The pressure sensor 120 shown in FIG. 15A and FIG. 15B detects vapor pressure generated when living tissues to be joined are heated and transmits a signal thereof to the pressure measuring portion 18a.

Various kinds of pressure sensors such as thin gauge, semiconductor strain gauge, piezoelectric, and optical fiber types are used as the pressure sensor 120, but the pressure sensor 120 is not limited to these types and any pressure sensor having a similar function can substitute.

Accordingly, the vapor pressure originating from living tissues to be joined can be measured precisely and the flow rate adjustment portion 20 can be controlled by the fluid control portion 18 in accordance with the vapor pressure. The pressure sensor 120 can measure not only the magnitude of pressure, but also the degree of change in pressure.

Next, operations of the treatment apparatus 10 according to the present embodiment will be described.

Energy is supplied to each of the first high-frequency electrode 54a and the second high-frequency electrode 54b from the energy source 14 to heat living tissues between the first high-frequency electrode 54a and the second high-frequency electrode 54b.

If the temperature of the living tissues to be joined rises, vapor is generated. The impedance Z of the held living tissues rises. Thus, it becomes difficult to proceed with treatment even if high-frequency energy is provided to the living tissues to be joined (to be welded, to be sealed). Thus, the vapor pressure (amount of generated vapor) of the living tissues to be joined is measured by the pressure sensor 120 and the pressure measuring portion 18a and a suitable conductive fluid in accordance with the pressure is fed from the first and second openings 56a and 56b. Then, the temperature of the living tissues is lowered (the impedance Z is lowered) to facilitate the supply of high-frequency energy.

According to the present embodiment, as described above, effects below can be achieved.

When high-frequency power is applied to living tissues to be joined held by the first and second holding bodies 52a and 52b, a conductive fluid can be fed in accordance with, in addition to the impedance Z, the state (vapor generation) of the living tissues to be joined (to be welded, to be sealed) by the treatment apparatus 10.

So, an increase in impedance Z can be inhibited solely in the living tissues to be joined held (gripped) between the electrodes (holding faces) 54a and 54b so that high-frequency energy can be effectively supplied to promote protein denaturation on the joining surface. Thus, for example, when living tissues are attempted to join together, a stronger joining force (tissue welding force, tissue sealing force) can be obtained.

Sixth Embodiment

Next, the sixth embodiment will be described. The present embodiment is a modification of the fourth and fifth embodiments and the same reference numerals are attached to the same members described in the fourth and fifth embodiments and a detailed description thereof is omitted here.

The treatment apparatus 10 in the sixth embodiment is obtained by replacing the pressure sensor 120 described in the fifth embodiment by a vapor recovery pipe (reference numeral 120 is attached for convenience) and other components such as the electro-surgical device (treatment device) 12, the energy source 14, the storage portion 16, the fluid control portion 18, the flow rate adjustment portion 20, and the pressure measuring portion 18a are the same. Thus, the sixth embodiment will be described using FIG. 14 to FIG. 15C used for the fourth and fifth embodiments.

The vapor recovery pipe 120 shown in FIG. 15A and FIG. 15B is provided in the high-frequency electrode 54a of the main body 62a of the first holding member 52a and (though not shown) the high-frequency electrode 54b of the main body 62b of the second holding member 52b. The vapor recovery pipe 120 recovers vapor originating when living tissues to be joined (to be welded, to be sealed) are heated. The vapor recovery pipe 120 discharges vapor out of the electro-surgical device 12 from a fluid discharge port via the shaft 34 and the handle 32 so that the amount of vapor can be measured by the pressure measuring portion 18a.

When compared with the fifth embodiment, the sixth embodiment is only different in that the vapor recovery pipe 120 is formed in place of the pressure sensor 120 of the holding portions 36 and other structures are the same as those of the fifth embodiment and thus, a detailed description of operations is omitted here. Vapor pressure recovered by the vapor recovery pipe 120 is measured at a place apart from the electro-surgical device (treatment device) 12. Accordingly, vapor pressure can be measured at a place apart from the holding portions 36, instead of the holding portions 36.

Seventh Embodiment

Next, the seventh embodiment will be described using FIG. 16A to FIG. 16C. The present embodiment is a modification of the second embodiment and the same reference numerals are attached to the same members described in the second embodiment and a detailed description thereof is omitted here.

As shown in FIG. 16A, a lid portion 132a is disposed in the main body 62a of the first holding member 52a. A plurality of high-frequency electrodes (joining treatment portion) 134a in a pin shape as output members or energy discharge parts are fixed to the lid portion 132a.

The main body 62a has a plurality of circular holes (fluid feed portion) 136a in which the high-frequency electrodes 134a are arranged and also a gap between the high-frequency electrodes 134a and the main body 62a is used for the flow of a conductive fluid formed as through infusion openings. The high-frequency electrodes 134a and the circular holes 136a are each arranged at regular intervals and the outside diameter of the high-frequency electrodes 134a is formed smaller than the inside diameter of the circular holes 136a. Thus, if the lid portion 132a is fixed to the main body 62a, each of the high-frequency electrodes 134a is disposed in the corresponding circular hole 136a. At this point, the central axis of each of the high-frequency electrodes 134a and that of the circular hole 136a match.

Hollow cylindrical barrier portions (holding face for living tissues) 138a are formed in the main body 62a. The circular hole 136a is formed on the central axis of the barrier portion 138a. The contact surface of each of the barrier portions 138a is formed at a position slightly higher than the surface of the high-frequency electrode 134a. Thus, the barrier portions 138a have a function similar to that of the barrier portions (dams) 116a and 116b in the second embodiment so that a fluid such as a liquid can be prevented from flowing out to peripheral tissues of living tissues to be joined.

Each of the circular holes 136a formed in a space between each of the barrier portions 138a and each of the high-frequency electrodes 134a is communicatively connected to a fluid feed pipe 140a. The fluid feed pipe 140a cuts through up to the side to separate from the first holding member 52a and is communicatively connected to the first duct 50a to be connected to the tube 28a via the shaft 34 and the handle 32. Incidentally, in addition to fluid feeding, the fluid feed pipe 140a is preferably suckable. If a fluid is suckable, an excessive fluid that does not penetrate into living tissues can be prevented from flowing into peripheral living tissues around living tissues to be joined (to be welded, to be sealed) by sucking such a fluid. Moreover, a fluid such as vapor originating as living tissues to be joined are denatured can be recovered while high-frequency power is applied to the living tissues. Thus, between the start and the end of a sequence of treatment (between the start and the end in FIG. 5 in the first embodiment), a fluid originating from living tissues and conductive fluid can be prevented from flowing into peripheral living tissues around living tissues to be joined by sucking such fluids through the circular holes 136a except when a conductive fluid is infused through the circular holes 136a using the flow rate adjustment portion 20 by the fluid control portion 18.

Eighth Embodiment

Next, the eighth embodiment will be described using FIG. 17A to FIG. 17C. The present embodiment is a modification of the seventh embodiment and the same reference numerals are attached to the same members described in the seventh embodiment and a detailed description thereof is omitted here.

As shown in FIG. 17B and FIG. 17C, the lid portion 132a is disposed in the main body 62a of the first holding member 52a. A plurality of high-frequency, electrodes (joining treatment portion) 142a in a needle shape as output members or energy discharge parts and also as localized protrusions are fixed to the lid portion 132a. The high-frequency electrodes 142a and the circular holes 136a are each arranged at regular intervals and the outside diameter of the base of the high-frequency electrodes 142a is formed smaller than the inside diameter of the circular holes 136a. Thus, if the lid portion 132a is fixed to the main body 62a, each of the high-frequency electrodes 142a is disposed in the corresponding circular hole 136a. At this point, the central axis of each of the high-frequency electrodes 142a and that of the circular hole 136a match.

Each of the circular holes 136a formed in a space between each of the barrier portions 138a and each of the high-frequency electrodes 142a is communicatively connected to the fluid feed pipe 140a. The fluid feed pipe 140a cuts through up to the side to separate from the first holding member 52a and is communicatively connected to the first duct 50a to be connected to the tube 28a via the shaft 34 and the handle 32.

The perimeter of the circular holes 136a is formed as a recess (holding face) 144a. Thus, a fluid is prevented from leaking out of the first holding member 52a. Then, ends (distal ends) of the plurality of high-frequency electrodes 142a in the needle shape protrude closer to the second holding member 52b than the edge 80a.

Thus, while it is difficult to directly feed a liquid except the surface of the first high-frequency electrode 54a by the first openings 56a in the first embodiment, a conductive fluid can be caused to penetrate into living tissues by providing the first and second high-frequency electrodes (joining treatment portion) 142a and 142b in the needle shape and causing a conductive fluid to flow toward held living tissues to be joined while the high-frequency electrodes 142a and 142b are punctured. Consequently, high-frequency energy can effectively be guided and even if the held living tissues are very thick, high-frequency energy can effectively be supplied to the central part and neighborhood of joining surface of the living tissues.

The main body 62b and the second high-frequency electrode 54b of the second holding member 52b need not be formed symmetrically with respect to the main body 62a and the first high-frequency electrode 54a of the first holding member 52a, and cases in which the high-frequency electrodes 142a of the first holding member 52a and the high-frequency electrodes 142b of the second holding member 52b are different in shape or disposed asymmetrically and the high-frequency electrodes 142a and 142b are alternately disposed are permitted.

Ninth Embodiment

Next, the ninth embodiment will be described using FIG. 18A and FIG. 18B. The present embodiment is a modification of the second and eighth embodiments and the same reference numerals are attached to the same members described in the second and eighth embodiments and a detailed description thereof is omitted here.

Figures 18A, 18B:
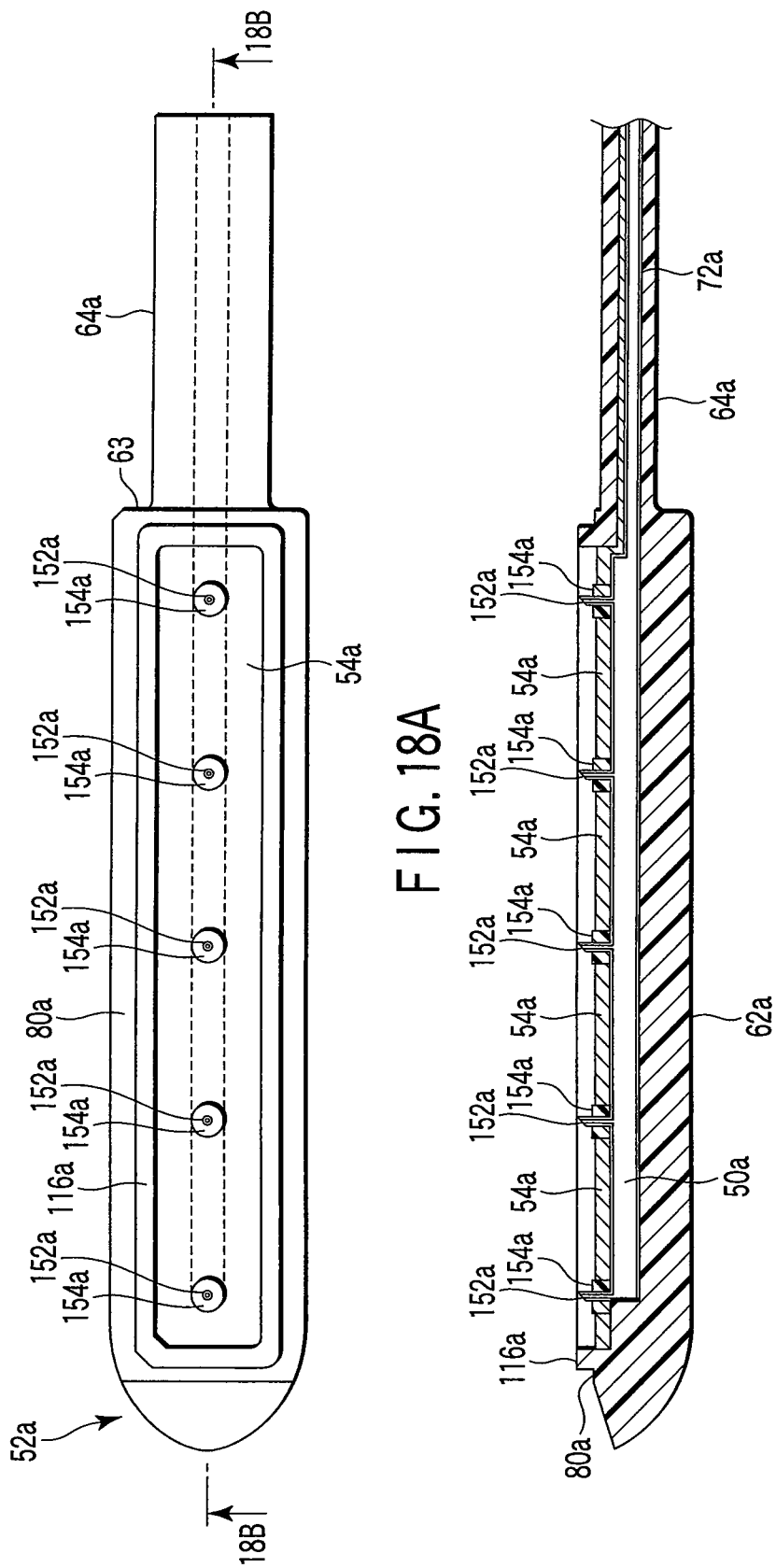
FIG. 18A is a schematic plan view showing the first holding member on the side nearer to the second holding member of the holding portion of the electro-surgical device of the treatment apparatus according to the ninth embodiment.
FIG. 18B is a schematic longitudinal sectional view showing the first holding member along a line 18B-18B shown in FIG. 18A of the holding portion of the electro-surgical device of the treatment apparatus according to the ninth embodiment.

As shown in FIG. 18A, first local injection needle parts (fluid feed portions) 152a are formed as localized protrusions in place of the first openings 56a. Each of the first local injection needle parts 152a is supported, for example, by a support member 154a having insulation properties, such as PTFE. Thus, the first local injection needle parts 152a are prevented from being bent by a large force applied when living tissues are punctured by the first local injection needle parts 152a.

Also, as shown in FIG. 18A and FIG. 18B, the tip of the first local injection needle parts 152a are positioned higher than the surface of the first high-frequency electrode 54a and are formed substantially as high as the contact surface of the first barrier portions (dams) 116a. Thus, when living tissues to be joined (to be welded, to be sealed) are held by the holding portions 36, the tip of the first local injection needle parts 152a is formed to be positioned inside the living tissues.

Though not shown, the main body 62b, the second high-frequency electrode 54b, and second local injection needle parts (fluid feed portions) 152b of the second holding member 52b are also formed symmetrically with respect to the main body 62a, the first high-frequency electrode 54a, and the first local injection needle parts 152a of the first holding member 52a. Thus, when the second holding member 52b is closed with respect to the first holding member 52a, the barrier portions (dams) 116a of the first holding member 52a and the local injection needle parts 152a, and the barrier portions (dams) 116b of the second holding member 52b and the local injection needle parts 152b are mutually brought into contact respectively, and a space is formed between the first high-frequency electrode 54a and the second high-frequency electrode 54b. That is, the local injection needle parts 152a and 152b can be arranged inside living tissues to be joined.

Thus, it is difficult to directly feed a liquid except the surface of the first high-frequency electrode 54a by the first openings 56a, but by providing the first and second local injection needle parts 152a and 152b, a conductive fluid can also be fed to the central part (in the axial direction of the local injection needle parts 152a and 152b) of held living tissues to be joined. Accordingly, high-frequency energy can effectively be guided and even if the held living tissues are very thick, high-frequency energy can effectively be supplied to the central part and neighborhood of the joining surface of the living tissues.

Moreover, the main body 62b and the second high-frequency electrode 54b of the second holding member 52b need not be formed symmetrically with respect to the main body 62a and the first high-frequency electrode 54a of the first holding member 52a, and cases in which the local injection needle parts 152a of the first holding member 52a and the local injection needle parts 152b of the second holding member 52b are different in shape or disposed asymmetrically and the local injection needle parts 152a and 152b are alternately disposed are permitted.

In the present embodiment, the first and second local injection needle parts 152a and 152b are not limited to a simple cylindrical shape and providing openings in the wall surface of the first and second local injection needle parts 152a and 152b is also permitted. Accordingly, a conductive fluid can uniformly be fed to the whole body of held tissues regardless of the thickness of the held tissues.

Next, operations of the treatment apparatus 10 according to the present embodiment will be described.

As described in the first embodiment, living tissues to be joined are held between the first holding member 52a and the second holding member 52b. At this point, the living tissues to be joined are punctured by the tips of the first and second local injection needle parts 152a and 152b and also the living tissues come into contact with the first high-frequency electrode 54a and the second high-frequency electrode 54b.

In this state, the foot switch or hand switch is operated. Then, energy is supplied to the first high-frequency electrode 54a and the second high-frequency electrode 54b from the high-frequency output device 26. On the other hand, a conductive fluid is fed to the first and second ducts 50a and 50b. Then, living tissues between the first high-frequency electrode 54a and the second high-frequency electrode 54b are heated.

When the living tissues to be joined (to be welded, to be sealed) are heated in this manner, the impedance Z of the held living tissues increases so that it gradually becomes difficult to supply energy. Thus, the impedance Z of the living tissues is forced to go down by infusing a conductive fluid from the first and second local injection needle parts 152a and 152b to facilitate the supply of energy.

If living tissues to be joined are very thick, only the surface of the living tissues may be heated so that an expected joining force is not obtained because the joining surface inside is not denatured. Thus, by feeding a conductive fluid up to the joining surface of the living tissues, using the first and second local injection needle parts 152a and 152b, the whole body of tissues can uniformly be heated including the joining surface even if the living tissues are thick.

According to the present embodiment, as described above, effects below can be achieved.

When a high-frequency current is applied to living tissues to be joined held by the first and second holding bodies 52a and 52b, a conductive fluid can be fed to the living tissues to be joined (to be welded, to be sealed) by the treatment apparatus 10. Moreover, the conductive fluid can be prevented from flowing into peripheral living tissues from the living tissues to be joined by the first and second barrier portions (dams) 116a and 116b and also the conductive fluid can uniformly be fed up to the central part of the living tissues to be joined. Then, high-frequency energy can uniformly be supplied to the whole body of held living tissues to be joined to promote denaturation of proteins near the joining surface so that a large joining force (tissue welding force, tissue sealing force) can be obtained. Moreover, a thermal effect can more reliably be prevented from spreading to peripheral tissues from living tissues to be joined to which high-frequency power is supplied for treatment of the living tissues, which is superior also in terms of healing of the living tissues after treatment.

That is, an electro-surgical device producing superior operation effects that are not known in conventional technology, such as providing the first and second barrier portions (dams) 116a and 116b to prevent heat damage to living tissues from being denatured around the living tissues to be joined, and further lowering the impedance Z of only predetermined portions also in the holding direction of the living tissues to be joined so that large high-frequency energy can locally be supplied can be provided.

Tenth Embodiment

Next, the tenth embodiment will be described using FIG. 19 to FIG. 21B. The present embodiment is a modification of the first to ninth embodiments and the same reference numerals are attached to the same members described in the first to ninth embodiments and a detailed description thereof is omitted here.

Figure 19:
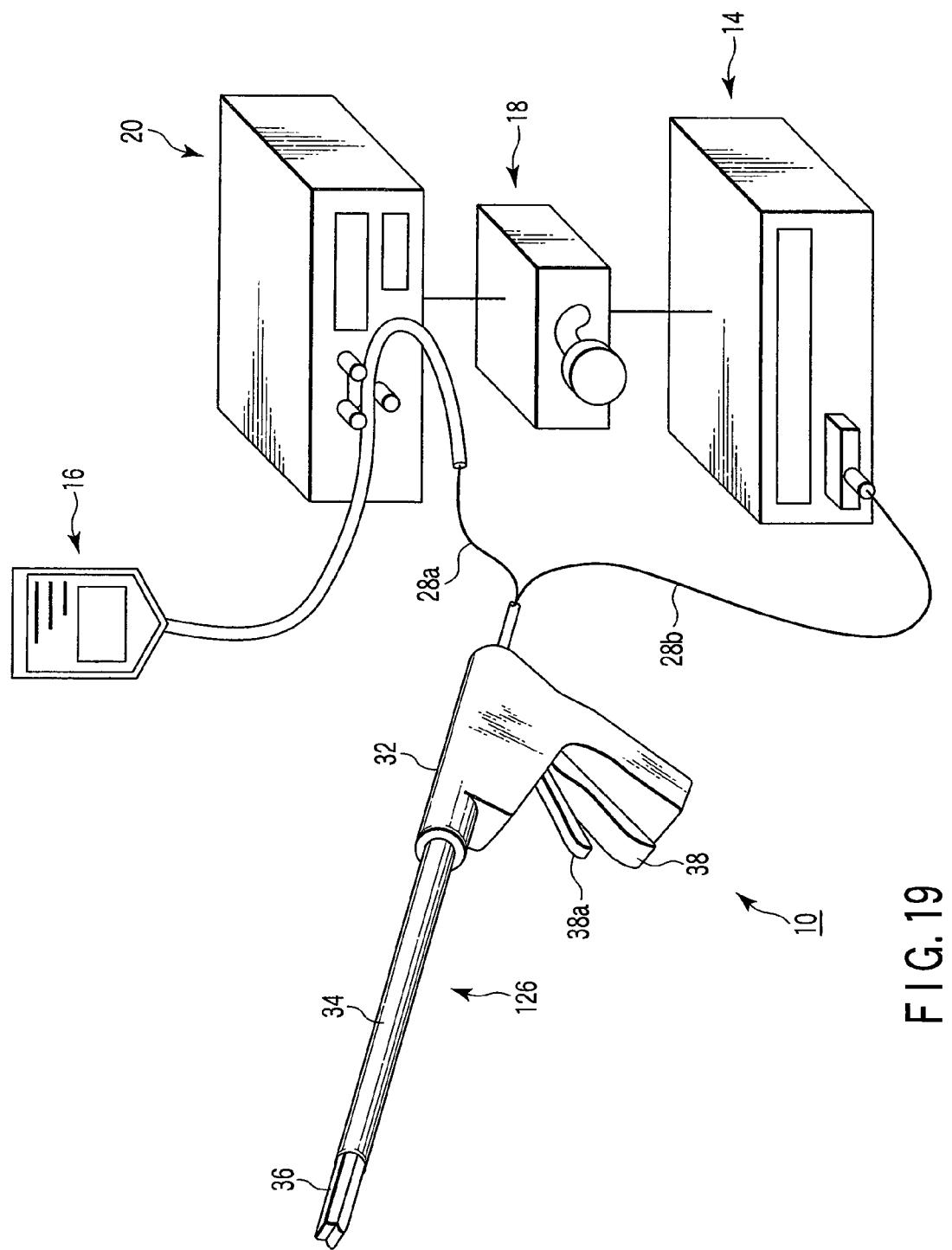
FIG. 19 is a schematic diagram showing a treatment apparatus according to the tenth embodiment.

As shown in FIG. 19, a cutter drive knob 38a is disposed in the handle 32 of an electro-surgical device (treatment device) 12b according to the present embodiment arranged together with the holding portion opening/closing knob 38.

Figure 20A:
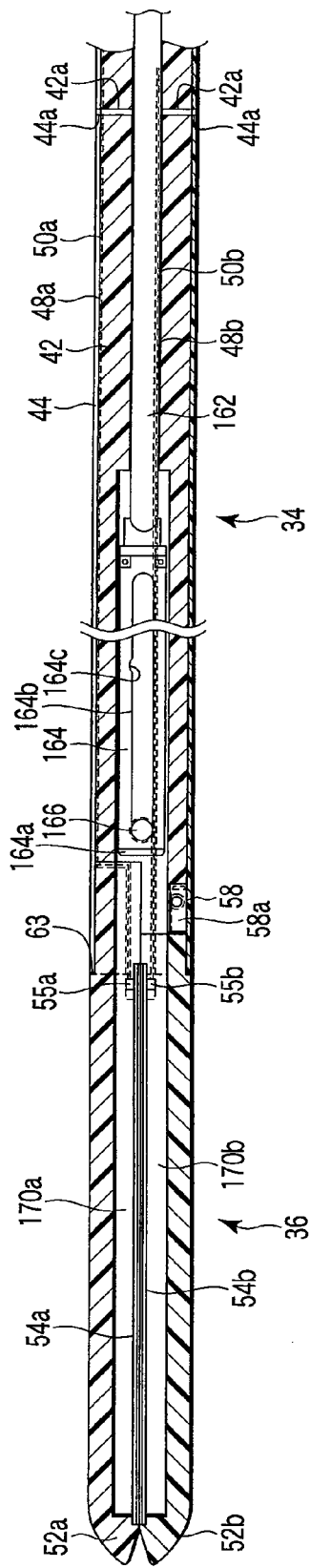
FIG. 20A is a schematic longitudinal sectional view showing a shaft of an electro-surgical device of the treatment apparatus and a holding portion having first and second holding members in a state where the holding portion is closed of the electro-surgical device of the treatment apparatus according to the tenth embodiment.
Figure 20B:
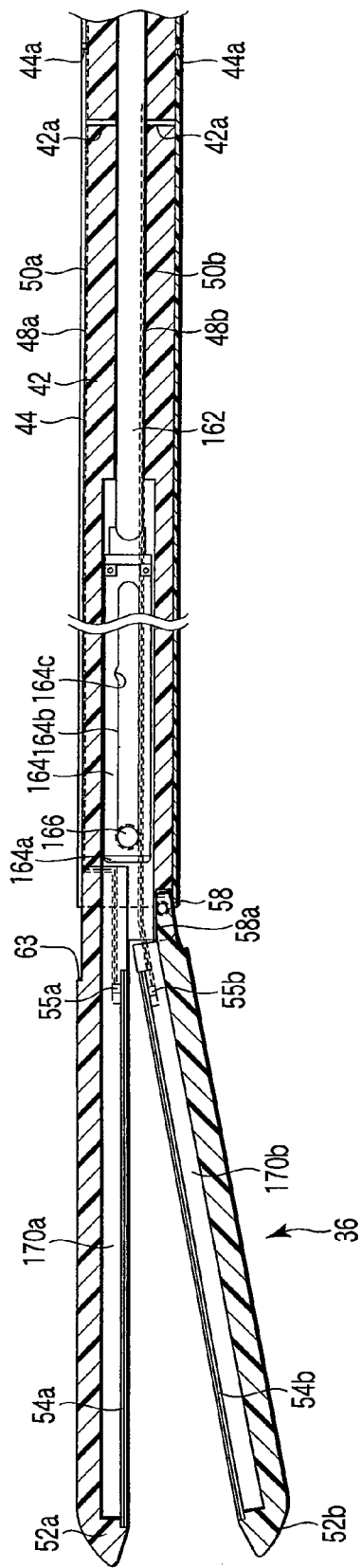
FIG. 20B is a schematic longitudinal sectional view showing the shaft of the electro-surgical device of the treatment apparatus and the first and second holding members in a state where the holding portion is opened of the electro-surgical device of the treatment apparatus according to the tenth embodiment.

As shown in FIG. 20A and FIG. 20B, a drive rod 162 is disposed movably in the axial direction thereof inside the cylinder 42 of the shaft 34. A thin-plate cutter (auxiliary treatment device) 164 is disposed at the tip of the drive rod 162. Thus, when the cutter drive knob 38a is operated, the cutter 164 moves via the drive rod 162.

The cutter 164 has a cutting edge 164a formed at the tip thereof and the tip of the drive rod 162 fixed to the base end thereof. A long groove 164b in which a movement control pin 166 is disposed is formed between the tip and base end of the cutter 164. The long groove 164b has an engaging portion 164c to engage the movement control pin 166 formed therein. The long groove 164b has the movement control pin 166 extending in a direction perpendicular to the axial direction of the shaft 34 fixed to the cylinder 42 of the shaft 34. Thus, the long groove 164b of the cutter 164 moves along the movement control pin 166. Consequently, the cutter 164 moves in a straight line. At this point, the cutter 164 is disposed in cutter guide grooves (fluid feed portions) 170a and 170b of the first holding member 52a and the second holding member 52b. The first high-frequency electrode 54a and the electrode arrangement portion 74a of the main body 62a of the first holding member 52a have the first cutter guide groove 170a formed to pass through the cutter 164. The first cutter guide groove 170a is also formed continuously in the base 64a of the first holding member 52a and further up to the handle 32 in the axial direction of the shaft 34.

Thus, the cutter 164 can move inside the first holding member 52a along the first cutter guide groove 170a. Similarly, the cutter 164 can move inside the second holding member 52b along the second cutter guide groove 170b.

As shown in FIG. 21A and FIG. 21B, the first openings 56a (See FIG. 4A and FIG. 4B) to feed a conductive fluid to living tissues to be joined (to be welded, to be sealed) are removed from the first high-frequency electrode 54a of the main body 62a of the first holding member 52a. To be able to feed a conductive fluid from the first cutter guide groove 170a as an infusion opening, the disposition of the first duct 50a is changed so that the first cutter guide groove 170a is connected to the tube 28a via the first duct 50a, the shaft 34, and the handle 32.

Incidentally, the cutter guide grooves 170a and 170b may also be used as a groove for suction. That is, a suction mechanism (not shown) is separately provided or the flow rate adjustment portion 20 acts also as a fluid sucking part. Thus, a conductive fluid that did not penetrate into living tissues to be joined can be recovered. Therefore, peripheral living tissues of the living tissues to be joined can be prevented from being affected.

Next, operations of the treatment apparatus 10 according to the present embodiment will be described.

As described in the first embodiment, living tissues to be joined (to be welded, to be sealed) are held between the first holding member 52a and the second holding member 52b. At this point, the contact surfaces of the first and second edges 80a and 80b are in close contact with living tissues and the living tissues are in contact with the first high-frequency electrode 54a and the second high-frequency electrode 54b.

In this state, the foot switch or hand switch is operated. High-frequency energy is supplied to the first high-frequency electrode 54a and the second high-frequency electrode 54b from the energy source 14. On the other hand, a fluid is fed to the first cutter guide groove 170a from the flow rate adjustment portion 20 via the tube 28a.

An operation to guide high-frequency energy is the same as that described in the first embodiment and thus, a detailed description thereof is omitted here.

The cutter 164 is used, for example, for cutting joined living tissues.

Here, as shown in FIG. 22A and FIG. 22B, a case in which, for example, enteric canals $I_{C1}$ and $I_{C2}$ of the small intestine are anastomosed using the treatment apparatus 10 having such operations will be described.

A pair of the enteric canals $I_{C1}$ and $I_{C2}$ arranged together is held by holding wall surfaces of both the enteric canals $I_{C1}$ and $I_{C2}$ using the main bodies 62a and 62b of the first and second holding bodies 52a and 52b. If, in this state, a pedal of the foot switch is pressed down, energy is supplied to the first and second high-frequency electrodes 54a and 54b. Then, the enteric canals $I_{C1}$ and $I_{C2}$ held between the first high-frequency electrode 54a of the first holding member 52a and the second high-frequency electrode 54b of the second holding member 52b are heated to denature the enteric canals $I_{C1}$ and $I_{C2}$. Thus, the wall surfaces of the enteric canals $I_{C1}$ and $I_{C2}$ are denatured.

Subsequently, when the impedance Z reaches the threshold (1000Ω), the supply of high-frequency energy is stopped and a conductive fluid is fed to the wall surfaces of the enteric canals $I_{C1}$ and $I_{C2}$.

By repeating such an operation, the living tissues of the enteric canals $I_{C2}$ and $I_{C2}$ are denatured to be joined (anastomosed) in a desired state.

Then, the supply of energy to the first and second high-frequency electrodes 54a and 54b is stopped and then, the cutter drive knob 38a shown in FIG. 19 is operated while the enteric canals $I_{C2}$ and $I_{C2}$ being held to advance the cutter 164 along the cutter guide grooves 170a and 170b from the state shown in FIG. 22A. As the cutter 164 advances, a region joined by being denatured by the electrodes 54a and 54b is cut. Then, the cutter 164 cuts an internal side of the region denatured to a substantially U shape (see the shape of the electrode 54a shown in FIG. 21A) by the electrodes 54a and 54b up to the neighborhood of the tip part thereof. Thus, a portion sealed in a substantially U shape of wall surfaces of the enteric canals $I_{C2}$ and $I_{C2}$ is cut so that the wall surfaces of the enteric canals $I_{C2}$ and $I_{C2}$ are communicatively connected. That is, the wall surfaces of the enteric canals $I_{C2}$ and $I_{C2}$ are anastomosed.

In this state, the holding portion opening/closing knob 38 of the handle 32 is operated to open the first and second holding bodies 52a and 52b. At this point, a first anastomosed part $A_{N1}$ on a mesentery M side and a second anastomosed part $A_{N2}$ on the opposite side of the mesentery M side are formed.

Further, the first and second holding bodies 52a and 52b are closed and the pedal of the foot switch is pressed down while ends of the enteric canals $I_{C1}$ and $I_{C2}$ are held to provide high-frequency energy. Thus, as shown in FIG. 22B, ends of the enteric canals $I_{C1}$ and $I_{C2}$ are denatured by the high-frequency electrodes 54a and 54b before being sealed. That is, a seal part $S_P$ is formed at the ends of the enteric canals $I_{C2}$ and $I_{C2}$. At this point, the cross section along the line 22A-22A shown in FIG. 22B is substantially in a state shown in FIG. 22A. Thus, the enteric canals $I_{C2}$ and $I_{C2}$ are anastomosed with ends thereof sealed by the seal part $S_P$.

Incidentally, an excessive portion of the seal part $S_P$ is cut off by the cutter 164 or the like.

According to the present embodiment, as described above, effects below can be achieved in addition to effects described in the first embodiment.

After applying high-frequency power to living tissues held by the holding member 52a, a conductive fluid can immediately be introduced into the first cutter guide groove 170a. That is, the first cutter guide groove 170a can be used to feed a fluid, instead of the first openings 56a. That is, the electrosurgical device 12b producing superior operation effects such as being able to use the first cutter guide groove 170a for the cutter 164 disposed to cut held living tissues simultaneously as the openings 56a to feed a fluid without providing the openings 56a to feed a fluid can be provided.

Eleventh Embodiment

Next, the eleventh embodiment will be described using FIG. 23 to FIG. 26B. Here, as an energy device, a circular-type bipolar electro-surgical device (treatment device) 12c to provide treatment, for example, through an abdominal wall or outside the abdominal wall is taken as an example to describe the eleventh embodiment.

As shown in FIG. 23, the electro-surgical device 12c includes a handle 232, a shaft 234, and holding portions 236 that can be opened and closed. The flow rate adjustment portion 20 is connected to the handle 232 via the tube 28a and the energy source 14 is connected to the handle 232 via the cable 28b.

A holding portion opening/closing knob 238 and a cutter drive lever 238a are disposed in the handle 232. The holding portion opening/closing knob 238 is disposed, for example, at a base end of the handle 232 and is rotatable with respect to the handle 232. If the holding portion opening/closing knob 238 is rotated, for example, clockwise with respect to the handle 232, a separating holding portion 244, described later, of the holding portions 236 separates from the main body side holding portion 242 (See FIG. 25B) and if rotated counterclockwise, the detachable side holding portion 244 approaches the main body side holding portion 242 (See FIG. 25A). The cutter drive lever 238a is formed to extend from the side of the handle 232 and is movable within a predetermined range in the axial direction of the handle 232.

The shaft 234 is formed in a cylindrical shape. In consideration of insertability into living tissues, the shaft 234 is suitably curved. Naturally, the shaft 234 may also be suitably formed to be straight.

Figures 24A, 24B:
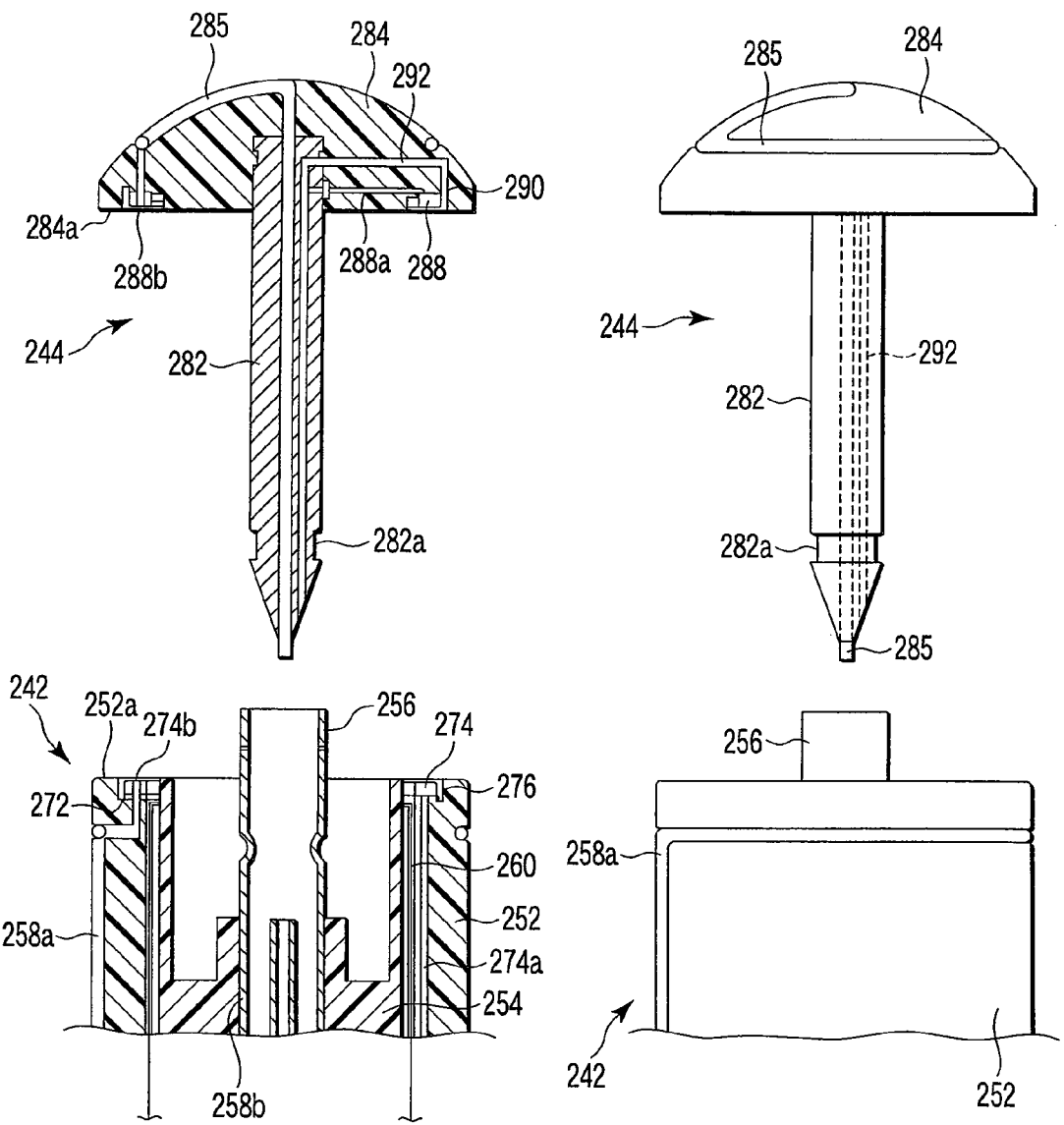
FIG. 24A is a schematic longitudinal sectional view showing the state in which a main body side holding portion and a detachable side holding portion of the electro-surgical device of the treatment apparatus according to the eleventh embodiment are separated.
FIG. 24B is a schematic diagram showing the state in which the main body side holding portion and the detachable side holding portion of the electro-surgical device of the treatment apparatus according to the eleventh embodiment are separated.

The holding portions 236 are disposed at the tip of the shaft 234. As shown in FIG. 24A and FIG. 24B, the holding portions 236 include the main body side holding portion 242, formed at the tip of the shaft 234, and the detachable side holding portion 244 that can be attached to and detached from the main body side holding portion 242.

The main body side holding portion 242 includes a cylindrical body 252, a frame 254 disposed inside the cylindrical body 252, a current-carrying pipe 256 disposed inside the frame 254, and fluid feed pipes 258a and 258b. The cylindrical body 252 and frame 254 have insulation properties. The cylindrical body 252 is coupled to the tip of the shaft 234 or formed integrally therewith. The fluid feed pipe 258a is disposed along the outside of the cylindrical body 252. The frame 254 is fixed to the cylindrical body 252.

Figures 25A, 25B:
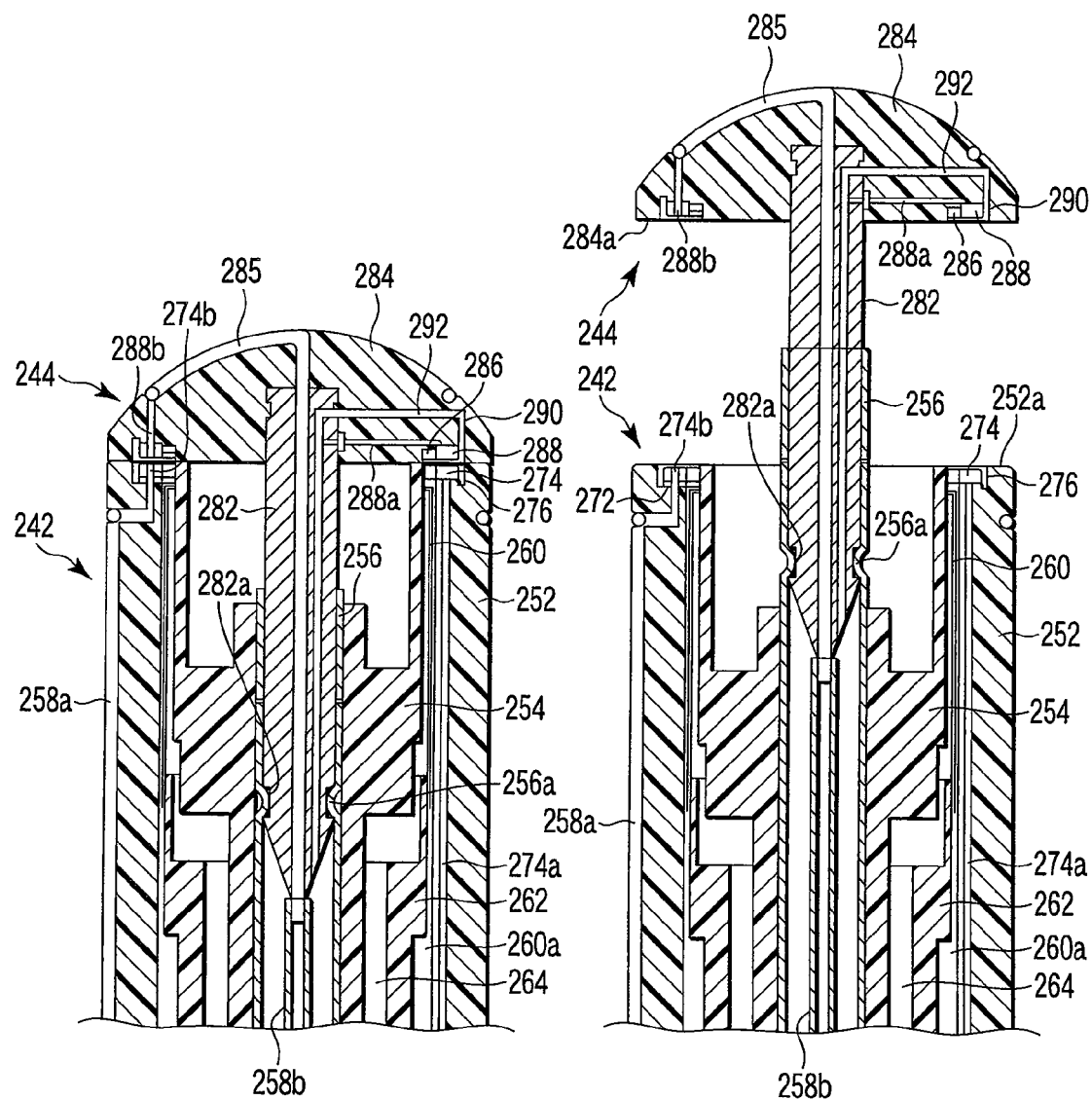
FIG. 25A is a schematic longitudinal sectional view showing the state in which the main body side holding portion and the detachable side holding portion of the electro-surgical device of the treatment apparatus are closed according to the eleventh embodiment.
FIG. 25B is a schematic longitudinal sectional view showing the state in which the main body side holding portion and the detachable side holding portion of the electro-surgical device of the treatment apparatus are opened according to the eleventh embodiment.

The central axis of the frame 254 is opened. The current-carrying pipe 256 is disposed in the opened central axis of the frame 254 movably within a predetermined range along the central axis of the frame 254. The fluid feed pipe 258b is disposed in the hollow central space of the current-carrying pipe 256. When the holding portion opening/closing knob 238 is rotated, as shown in FIG. 25A and FIG. 25B, the current-carrying pipe 256 and the fluid feed pipe 258b are integrally movable within a predetermined range, for example, by action of a ball screw (not shown). The current-carrying pipe 256 has a protrusion 256a protruding inward in the diameter direction formed so that a connector part 282a of a current-carrying shaft 282, described later, of the detachable side holding portion 244 is detachable. When the current-carrying shaft 282 is engaged with the current-carrying pipe 256, a fluid feed pipe 285, described later, of the detachable side holding portion 244 is connected to the fluid feed pipe 258b.

As shown in FIG. 25A and FIG. 25B, a space (a cutter groove 260a) is formed between the cylindrical body 252 and the frame 254. A cylindrical cutter 260 is disposed in the space (the cutter groove 260a). The base end of the cutter 260 is connected to the tip part of a pusher 262 for a cutter disposed inside the shaft 234. The inner circumferential surface of the base end of the cutter 260 is fixed to the outer circumferential surface of the pusher 262 for a cutter. Though not shown, the base end of the pusher 262 for a cutter is connected to the cutter drive lever 238a of the handle 232. Thus, if the cutter drive lever 238a is operated with respect to the handle 232, the cutter 260 moves via the pusher 262 for a cutter.

A first fluid discharge conduit 264 is formed between the pusher 262 for a cutter and the frame 254. Then, the shaft 234 or the handle 232 has a fluid discharge port (not shown) through which a fluid via the first fluid discharge conduit (fluid path) 264 is discharged to the outside formed therein.

As shown in FIG. 24A and FIG. 24B, a first electrode arrangement part 272 in an annular shape is formed at the tip of the cylindrical body 252. In the first electrode arrangement part 272, a first high-frequency electrode (joining treatment portion) 274 as an output member or energy discharge part is disposed. The tip of a first current-carrying line 274a is fixed to the first high-frequency electrode 274. The first current-carrying line 274a is connected to the cable 28b via the main body side holding portion 242, the shaft 234, and the handle 232.

A fluid discharge prevention groove 276 is formed annularly outside the first high-frequency electrode 274. The fluid discharge prevention groove 276 is communicatively connected to the first fluid discharge conduit 264 via the cutter groove 260a.

The detachable side holding portion 244 includes, on the other hand, the current-carrying shaft 282 having the connector part 282a, a head part 284, and the fluid feed pipe 285. The current-carrying shaft 282 has a circular cross section and is formed in a tapering shape at one end with the other end fixed to the head part 284. The connector part 282a is formed in a concave groove shape that can be engaged with the protrusion 256a of the current-carrying pipe 256. Except for the connector part 282a of the current-carrying shaft 282, the outer surface thereof is insulated by a coating or the like.

A cutter receiver 286 is disposed annularly in the head part 284. A second high-frequency electrode (joining treatment portion) 288 in an annular shape is formed outside the cutter receiver 286. One end of a second current-carrying line 288a as an output member or energy discharge part is fixed to the second high-frequency electrode 288. The other end of the second current-carrying line 288a is electrically connected to the current-carrying shaft 282. A fluid discharge prevention groove 290 is formed annularly outside the second high-frequency electrode 288.

Further, the fluid discharge prevention groove 290 is communicatively connected to a second fluid discharge conduit 292 of the head part 284 and the current-carrying shaft 282. The second fluid discharge conduit 292 is communicatively connected to the current-carrying pipe 256, leading to the shaft 234 and the handle 232. The shaft 234 or the handle 232 has a fluid discharge port (not shown), through which a fluid is discharged to the outside, formed therein.

The current-carrying pipe 256 is connected to the cable 28b via the shaft 234 and the handle 232. Thus, when the connector part 282a of the current-carrying shaft 282 of the detachable side holding portion 244 is engaged with the protrusion 256a of the current-carrying pipe 256, the second high-frequency electrode 288 and the current-carrying pipe 256 are electrically connected.

The first high-frequency electrode 274 has first openings (fluid feed portion) 274b formed as infusion openings, and a fluid is fed from these openings 274b. The first openings 274b are disposed in the annular first high-frequency electrode 274 at predetermined intervals. Each of the openings 274b is connected to the tube 28a via the fluid feed pipe 258a, the shaft 234, and the handle 232.

Similarly, the second high-frequency electrode 288 also has second openings (fluid feed portion) 288b formed as infusion openings, and a fluid is fed from these openings 288b. The second openings 288b are disposed in the annular second high-frequency electrode 288 at predetermined intervals. Each of the openings 288b is connected to the tube 28a via the fluid feed pipe 285, the fluid feed pipe 258b, the shaft 234, and the handle 232.

Therefore, a conductive fluid is fed to living tissues to be joined (to be welded, to be sealed) held between the main body side holding portion 242 and the detachable side holding portion 244 based on settings of the treatment apparatus 10 by controlling the flow rate adjustment portion 20.

Next, operations of the treatment apparatus 10 according to the present embodiment will be described.

As shown in FIG. 23 and FIG. 25A, for example, the holding portions 236 and the shaft 234 of the electro-surgical device 12c are inserted through the abdominal wall when the main body side holding portion 242 is closed with respect to the detachable side holding portion 244. A space between the main body side holding portion 242 and the detachable side holding portion 244 of the electro-surgical device 12c is brought opposite to living tissues to be treated.

The holding portion opening/closing knob 238 of the handle 232 is operated to hold the living tissues to be treated by the main body side holding portion 242 and the detachable side holding portion 244. At this point, the holding portion opening/closing knob 238 is rotated, for example, clockwise with respect to the handle 232. Then, as shown in FIG. 25B, the current-carrying pipe 256 is moved to the tip side of the frame 254 of the shaft 234. Thus, the main body side holding portion 242 and the detachable side holding portion 244 are opened so that the detachable side holding portion 244 can be separated from the main body side holding portion 242.

Then, the living tissues to be treated are arranged between the first high-frequency electrode 274 of the main body side holding portion 242 and the second high-frequency electrode 288 of the detachable side holding portion 244. The current-carrying shaft 282 of the detachable side holding portion 244 is inserted into the current-carrying pipe 256 of the main body side holding portion 242. In this state, the holding portion opening/closing knob 238 of the handle 232 is rotated, for example, counterclockwise. Thus, the detachable side holding portion 244 is closed with respect to the main body side holding portion 242. In this manner, the living tissues to be joined are held between the main body side holding portion 242 and the detachable side holding portion 244.

At this point, the living tissues to be joined come into contact with the first high-frequency electrode 274 and the second high-frequency electrode 288.

In this state, the foot switch or hand switch is operated. Energy is supplied to the first high-frequency electrode 274 and the second high-frequency electrode 288 from the energy source 14 via the cable 28b. A conductive fluid is fed to the first and second openings 274b and 288b via the fluid feed pipes 258a, 258b, and 285.

The first high-frequency electrode 274 passes a high-frequency current to the second high-frequency electrode 288 via the living tissues. Thus, the living tissues held between the first high-frequency electrode 274 and the second high-frequency electrode 288 are heated.

When the living tissues to be joined are heated in this manner, the impedance of the held living tissues increases so that it becomes difficult to supply high-frequency energy. Thus, as described in the first embodiment, while the supply of high-frequency power is stopped after the impedance $Z$ reaches the threshold, a conductive fluid is infused for a penetration from the first and second openings 274b and 288b to force the impedance $Z$ of the living tissues when high-frequency power is supplied to the living tissues to be joined to go down to facilitate the supply of high-frequency power to the living tissues to be joined.

Like the linear-type electro-surgical device 12 described in the first embodiment, the circular-type electro-surgical device 12c according to the present embodiment may also heat living tissues around the living tissues to be joined in outside of the holding portion 236 when a conductive fluid is fed to lower the impedance $Z$ because the conductive fluid flows out into the surrounding living tissues.

A liquid such as an excessively fed conductive fluid and a liquid originating from living tissues flow into the fluid discharge prevention groove 276 of the main body side holding portion 242 and the fluid discharge prevention groove 290 of the detachable side holding portion 244. At this point, the contact surfaces of edges 252a and 284a of the main body side holding portion 242 and the detachable side holding portion 244 are in close contact with the living tissues to be joined, and thus the edges 252a and 284a and the fluid discharge prevention grooves 276 and 290 of the main body side holding portion 242 and the detachable side holding portion 244, respectively, serve as grooves to prevent a liquid from leaking out.

Thus, a fed liquid and a liquid originating from living tissues flow into the fluid discharge prevention grooves 276 and 290 of the main body side holding portion 242 and the detachable side holding portion 244 and then the fluid flows toward the first fluid discharge conduit 264 communicatively connected to the first fluid discharge prevention groove 276 and the second fluid discharge conduit 292 communicatively connected to the second fluid discharge prevention groove 290 at the tip of the detachable side holding portion 244. Then, the fluid is discharged to the outside of the electro-surgical device 12c through the first fluid discharge conduit 264 and the second fluid discharge conduit 292 via the shaft 234 and the handle 232.

The cutter 260 is formed in a cylindrical shape inside the electrode 274 and is used for cutting joined portions of living tissues and the like. By using the cutter 260, a hole of a predetermined diameter is formed.

Figure 26A:
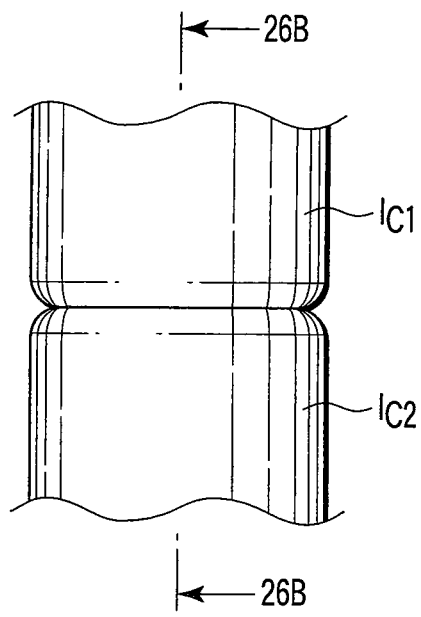
FIG. 26A is a schematic diagram showing the state of enteric canals joined together using the electro-surgical device according to the eleventh embodiment.
Figure 26B:
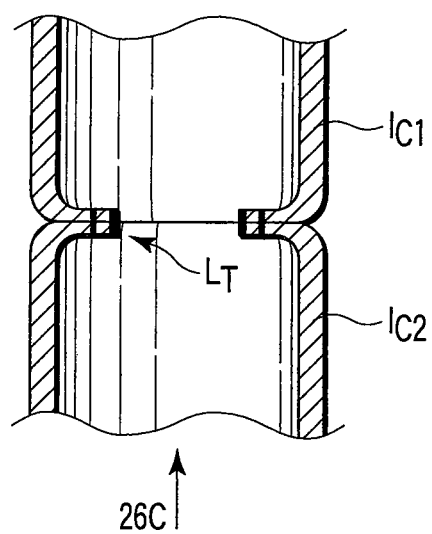
FIG. 26B is a schematic longitudinal sectional view along a line 26B-26B in FIG. 26A showing the state of enteric canals joined together using the electro-surgical device according to the eleventh embodiment.
Figure 26C:
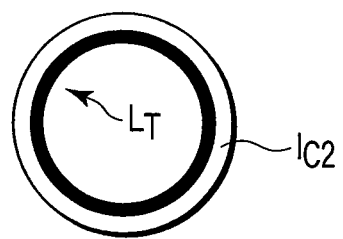
FIG. 26C is a schematic diagram showing the state observed from an arrow 26C direction in FIG. 26B when enteric canals are joined together using the electro-surgical device according to the eleventh embodiment.

Here, as shown in FIG. 26A to FIG. 26C, a case in which, for example, enteric canals $I_{C1}$ and $I_{C2}$ of a small intestine arranged together in the axial direction are joined to a sealed state using the treatment apparatus 10 having such operations will be described.

A pair of the enteric canals $I_{C2}$ and $I_{C2}$ arranged side by side in the axial direction are held by holding wall surfaces of both ends of the enteric canals $I_{C1}$ and $I_{C2}$ using the edge 252a and the high-frequency electrode 274 of the main body side holding portion 242 and the edge 284a and the high-frequency electrode 288 of the detachable side holding portion 244.

If, in this state, the pedal of the foot switch is pressed down, high-frequency energy is supplied to living tissues $L_T$ between the high-frequency electrodes 274 and 288. Thus, the enteric canals $I_{C1}$ and $I_{C2}$ are heated by these high-frequency electrodes 274 and 288 to denature the enteric canals $I_{C2}$ and $I_{C2}$.

Then, when the living tissues $L_T$ between the high-frequency electrodes 274 and 288 reach the predetermined threshold (1000Ω), output of high-frequency power is stopped and a conductive fluid is fed to the wall surfaces of the enteric canals $I_{C2}$ and $I_{C2}$.

By repeating such an operation, the living tissues of the enteric canals $I_{C1}$ and $I_{C2}$ are denatured before being joined (anastomosed) in a sealed state.

Then, the cutter drive knob 238a shown in FIG. 23 is operated while the enteric canals $I_{C2}$ and $I_{C2}$ are held between the main body side holding portion 242 and the detachable side holding portion 244 to advance the cutter 260 along the cutter guide groove 260a from the state shown in FIG. 24B, FIG. 25A, and FIG. 25B. As the cutter 260 advances, the internal side of a region joined after being denatured by the first high-frequency electrode 274 and the second high-frequency electrode 288 is cut in a circular shape by the cutting edge at the tip thereof. Thus, as shown in FIG. 26C, a portion sealed in a substantially circular shape of wall surfaces of the enteric canals $I_{C2}$ and $I_{C2}$ is cut to ensure a communicative state in a circular shape between the enteric canals $I_{C1}$ and $I_{C2}$.

In this state, the cutter drive knob 238a is operated to retract the cutter 260. Subsequently, the holding portion opening/closing knob 238 of the handle 232 is operated to open the main body side holding portion 242 and separating holding portion 244.

According to the present embodiment, as described above, the effects below can be achieved.

When a high-frequency current is passed to living tissues to be joined (to be welded, to be sealed) held by the holding portions 236, a conductive fluid can be fed to the living tissues to be joined by the treatment apparatus 10. Moreover, the conductive fluid can be inhibited from flowing into peripheral living tissues from the living tissues to be joined by the fluid discharge prevention grooves 276 and 290.

Thus, a fed liquid and a liquid originating from organisms can be discharged to the outside of the electro-surgical device 12c from the fluid discharge port through the fluid discharge conduit 264 formed between the first high-frequency electrode 274 and the edge 252a of the main body side holding portion 242 and between the frame 254 and the pusher 262 for a cutter via the shaft 234 and the handle 232.

Further, such a liquid can be discharged to the outside of the electro-surgical device 12c from the fluid discharge port through the fluid discharge prevention groove 290 formed between the second high-frequency electrode 288 and the edge 284a of the detachable side holding portion 244 via the second fluid discharge conduit 292, the shaft 234 and the handle 232.

Therefore, a fluid can be prevented from leaking out to peripheral living tissues of living tissues held between the holding portions 236.

Thus, it becomes possible to inhibit an increase in the impedance Z of solely held living tissues to be joined, supply high-frequency energy effectively, and promote denaturation of proteins so that a large joining force (tissue welding force, tissue sealing force) can be obtained. Moreover, a thermal effect can more reliably be prevented from spreading to peripheral tissues from living tissues to be joined to which high-frequency power is supplied for treatment of the living tissues while a conductive fluid is fed, which is superior also in terms of healing of the living tissues after treatment.

As described above, the fluid feed pipes 258a, 258b, and 285 are provided so that a conductive fluid is infused into living tissues from the first openings 274b of the main body side holding portion 242 shown in FIG. 25B and a conductive fluid is infused into living tissues from the second openings 288b of the detachable side holding portion 244. However, for example, the fluid feed pipes 258b and 285 may be removed. Or, instead of the fluid feed pipes 258b and 285, the fluid feed pipe 258a may be removed. That is, providing one of the first openings 274b of the main body side holding portion 242 and the second openings 288b of the detachable side holding portion 244 is enough.

Twelfth Embodiment

Next, the twelfth embodiment will be described using FIG. 27A and FIG. 27B. The present embodiment is a modification of the eleventh embodiment and the same reference numerals are attached to the same members described in the eleventh embodiment and a detailed description thereof is omitted here.

As shown in FIG. 27A and FIG. 27B, first local injection needle parts (fluid feed portions) 274c are formed as localized protrusions in place of the first openings 274b. The tip of the first local injection needle parts 274c is positioned higher than the surface of the first high-frequency electrode 274. Similarly for the detachable side holding portion 244, second local injection needle parts (fluid feed portions) 288c are formed as localized protrusions in place of the second openings 288b. Other components are the same as those in the eleventh embodiment shown in FIG. 24A to FIG. 25B and thus, a description thereof is omitted here.

Next, operations of the treatment apparatus 10 according to the present embodiment will be described.

Basically, operations are the same as those of the seventh embodiment. The present embodiment is different from the seventh embodiment in that the first local injection needle parts 274c are formed in place of the first openings 274b. As described in the seventh embodiment, living tissues to be joined (to be welded, to be sealed) are held between the main body side holding portion 242 and the detachable side holding portion 244. At this point, the living tissues are punctured by the tips of the first and second local injection needle parts 274c and 288c and also the living tissues are brought into contact with the first high-frequency electrode 274 and the second high-frequency electrode 288.

When the living tissues to be joined in this state are heated and denatured, the impedance of the held living tissues increases so that it becomes difficult for the current to flow. Thus, the impedance of the living tissues is forced to go down by infusing a fluid from the first and second local injection needle parts 274c and 288c to facilitate the supply of power.

If, at this point, the living tissues to be joined are very thick, only the surface of the living tissues may be heated without the inner part thereof being denatured. Thus, by feeding a conductive fluid into the inner part of the living tissues by the first and second local injection needle parts 274c and 288c, the living tissues can uniformly be heated regardless of the thickness of the tissues.

According to the present embodiment, as described above, the effects below can be achieved.

When a high-frequency current is passed to living tissues to be joined (to be welded, to be sealed) held by the main body side holding portion 242 and the detachable side holding portion 244, a fluid can be fed to the living tissues to be joined by the treatment apparatus 10. Moreover, the liquid can be prevented from flowing into peripheral living tissues from the living tissues to be joined by the first and second fluid discharge prevention grooves 276 and 290 and the first and second edges 252a and 284a and also the conductive fluid can uniformly be fed up to the central part, regardless of thickness of the living tissues to be joined.

Thus, high-frequency energy can uniformly be supplied to the whole body of held living tissues to be joined in order to promote denaturation of proteins at the joining surface so that a large joining force (tissue welding force, tissue sealing force) can be obtained.

Incidentally, as shown in FIG. 27A and FIG. 27B, the first local injection needle parts 274c are provided in the detachable side holding portion 244, and the second local injection needle parts 288c are provided in the main body side holding portion 242, but it is also preferable to provide one of the first local injection needle parts 274c of the detachable side holding portion 244 and the second local injection needle parts 288c of the main body side holding portion 242.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment apparatus to treat living tissues by applying energy to the living tissues, the treatment apparatus comprising:
   a pair of holding faces configured to hold the living tissues;
   a joining treatment portion arranged in at least one of the pair of holding faces to join the living tissues held between the pair of holding faces by energy repetitively supplied from an energy source; a detection portion which is configured to detect, through the joining treatment portion, living information of the living tissues;
   a fluid feed portion configured disposed on at least one of the holding faces of the pair of holding faces to feed fluid to the living tissues held between the pair of holding faces,
   an energy control portion configured to firstly stop supply of the energy to the living tissues, when the living information of the living tissues, detected by the detection portion, reaches a predetermined first impedance, and is configured to secondly stop supply of the energy to the living tissues, when the living information reaches a predetermined second impedance, which is larger than the first impedance;
   and a fluid control portion configured to control the fluid feed portion, the fluid control portion being configured to control the fluid feed portion to supply the fluid, from the fluid feed portion, to the living tissues, held between the pair of holding faces, every time the control portion stops the supply of energy to the living tissues.

2. The treatment apparatus according to claim 1, wherein the fluid feed portion includes infusion openings on the holding faces to feed the fluid to the living tissues held between the pair of holding faces.

3. The treatment apparatus according to claim 1, wherein the fluid feed portion includes openings provided around the treatment portion and infuses the fluid fed through the openings into the living tissues held between the pair of holding faces.

4. The treatment apparatus according to claim 1, wherein at least one localized protrusion protruding with respect to the holding face is provided on the fluid feed portion and the localized protrusion feeds the fluid into the living tissues held between the pair of holding faces.

5. The treatment apparatus according to claim 1, wherein the fluid feed portion includes at least one of a groove and a wall on the holding face to prevent the fluid from being fed to living tissues around the living tissues held between the pair of holding faces.

6. The treatment apparatus according to claim 1, wherein the detection portion sets at least one of a current, voltage, power, impedance, and phase information detected through the treatment portion as a threshold, and the fluid control portion controls feeding of the fluid from the fluid body feed portion based on the threshold.

7. The treatment apparatus according to claim 1, wherein at least one of a conductive fluid and a conductive gelatinized body is used as the fluid.

8. The treatment apparatus according to claim 1, wherein at least one of a pressure sensor and a temperature sensor is provided on the holding face and at least one of the pressure sensor and the temperature sensor detects progress of treatment for the living tissues held between the pair of holding faces.

9. The treatment apparatus according to claim 1, further comprising a pressure sensor which detects vapor pressure from the living tissues held between the pair of holding faces at a position apart from the holding faces.

10. The treatment apparatus according to claim 1, wherein the control portion restarts supplying the energy from the energy source to the treatment portion with a preset idle period after the control portion has finished the fluid supply from the fluid feed portion to the living tissue.

11. The electro-surgical device according to claim 1, wherein the electrode is configured to dehydrate the living tissues when supplying the energy to the living tissues.

12. The electro-surgical device according to claim 1, wherein the control portion is configured to control the energy such that the energy supplied to the living tissues when the first impedance is set as threshold can be higher than the energy supplied to the living tissues when the second impedance which is larger than the first impedance is set as threshold.

13. The electro-surgical device according to claim 1, wherein the energy is high frequency energy.

14. An electro-surgical device configured to join living tissues, comprising:
   a pair of holding faces which is configured to hold the living tissues;
   an electrode which is provided on at least one of the pair of holding faces to repetitively supply energy to the living tissues held by the pair of holding faces and be able to detect living information of the living tissues held by the pair of holding faces, and which is configured to firstly stop supply of the energy to the living tissues, when the living information reaches a predetermined first impedance, and is configured to secondly stop supply of the energy to the living tissues when the living information reaches a predetermined second impedance, which is larger than the first impedance; and
   a fluid feed portion which is provided on at least one of the holding face or the electrode, which is able to feed a conductive fluid to the living tissues held by the pair of holding faces, and which is configured to supply the fluid to the living tissues every time the electrode stops the supply of energy to the living tissues.

15. The electro-surgical device according to claim 14, wherein the fluid feed portion includes openings through which fluid is passed to the holding face provided around a treatment portion.

16. The electro-surgical device according to claim 14, wherein
the fluid feed portion includes at least one localized protrusion protruding with respect to the holding face.

17. The electro-surgical device according to claim 14, wherein
the holding face includes at least one of a groove and a wall and at least one of the groove and the wall prevents the fluid bodies from flowing out of the holding face.

18. The electro-surgical device according to claim 14, wherein the electrode is configured to dehydrate the living tissues when supplying the energy to the living tissues.

19. The electro-surgical device according to claim 14, wherein the electrode is configured to supply the energy to the living tissues, and wherein the energy supplied to the living tissues when the first impedance is set as threshold is higher than the energy supplied to the living tissues when the second impedance which is larger than the first impedance is set as threshold.

20. The electro-surgical device according to claim 14, wherein the energy is high frequency energy.

* * * * *